United States Patent [19]

McLafferty et al.

[11] 4,008,388
[45] Feb. 15, 1977

[54] MASS SPECTROMETRIC SYSTEM FOR RAPID, AUTOMATIC AND SPECIFIC IDENTIFICATION AND QUANTITATION OF COMPOUNDS

[75] Inventors: Fred W. McLafferty, Ithaca, N.Y.; Robert H. Hertel, Pasadena; Robert D. Villwock, Glendora, both of Calif.

[73] Assignee: Universal Monitor Corporation, Pasadena, Calif.

[22] Filed: Aug. 4, 1975

[21] Appl. No.: 601,825

Related U.S. Application Data

[63] Continuation of Ser. No. 470,642, May 16, 1974, abandoned.

[52] U.S. Cl. .................... 235/151.35; 250/281
[51] Int. Cl.² .................... G06F 15/52; G06G 7/74
[58] Field of Search .................... 235/151.3, 151.35; 73/23.1; 250/281, 294, 299; 356/98

[56] References Cited
UNITED STATES PATENTS

| | | |
|---|---|---|
| 3,012,139 | 12/1961 | Hanson et al. .................... 250/281 X |
| 3,154,747 | 10/1964 | Kendall .................... 250/281 X |
| 3,493,742 | 2/1970 | Martignoni et al. .......... 235/151.35 |
| 3,624,420 | 11/1971 | Krutz et al. .................... 250/281 X |
| 3,639,741 | 2/1972 | Carrick .................... 250/281 X |
| 3,723,713 | 3/1973 | Banner et al. ................ 225/151.35 |

*Primary Examiner*—Jerry Smith

[57] ABSTRACT

An automated mass spectrometric system which is capable of analyzing and identifying a wide variety of chemical compounds. A sample of an unknown compound, in liquid, solid or gaseous state, is introduced into the invented system. It may be a pure sample or a mixture of compounds. In either case, its mass spectrum is searched for selected peaks and an attempt is made to match such peaks to previously stored, characteristic spectra of one or more compounds in a predetermined family of compounds. Matching is on a probabilistic basis, reflecting the occurrence probabilities or uniqueness of the mass peaks found, and the accuracy with which the relative peak intensity pattern matches that of any of the compounds in the family of compounds sought. If one or more of the compounds in the family of compounds is identified as being present in the sample, its quantity is also determined automatically by the invention. Moreover a confidence index is generated as a measure of the likelihood that the compound identified as being present is in fact present.

The present invention comprises a sample inlet device, preferably a flash evaporator and separator, a mass spectrometer, electronic means for controlling the operation of the mass spectrometer and electronic means for analyzing the mass peaks for identification. Based upon the results of data analysis, i.e., matching of spectra, the analysis means provides signals to the control means to alter the data acquisition, in closed loop fashion. System sensitivity and other operating parameters are automatically varied as required to obtain accurate mass peak measurements.

46 Claims, 13 Drawing Figures

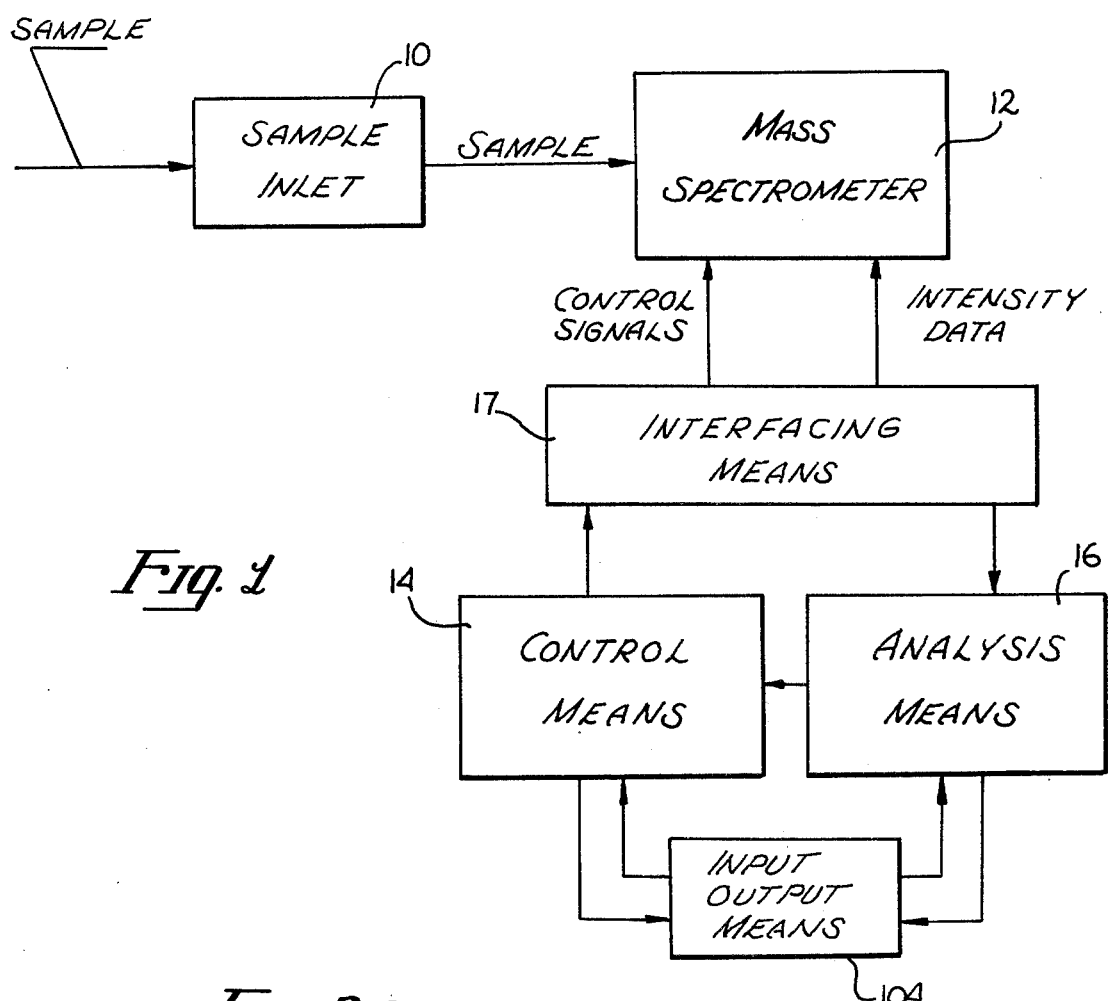
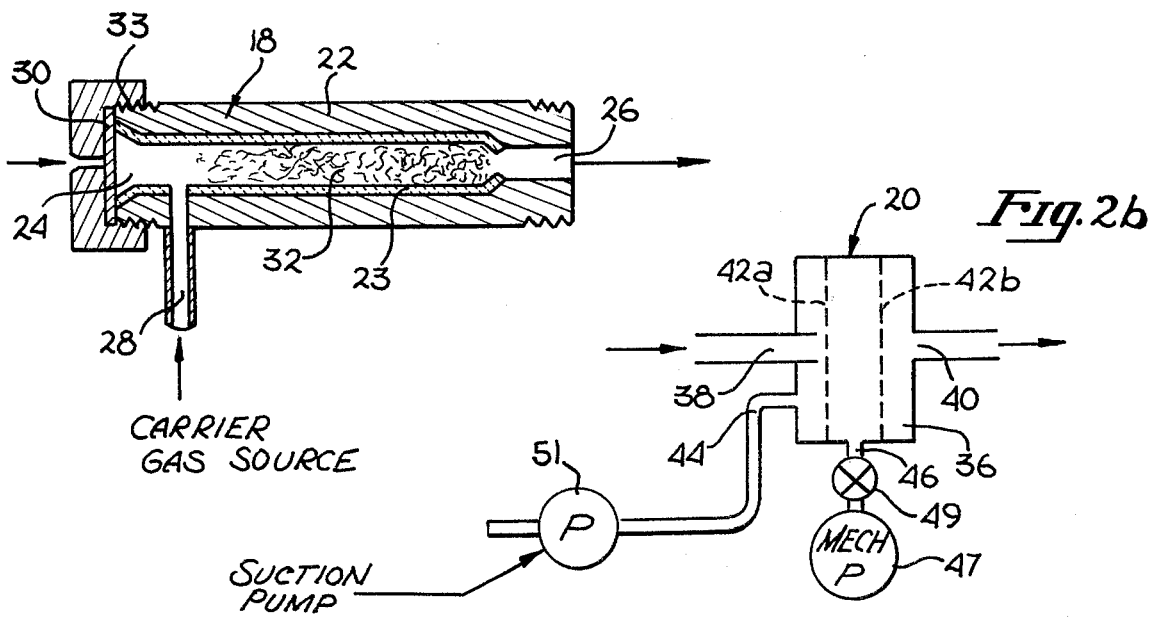

MASS SPECTROMETRIC SYSTEM FOR RAPID, AUTOMATIC AND SPECIFIC IDENTIFICATION AND QUANTITATION OF COMPOUNDS

This is a continuation of application Ser. No. 470,642, filed May 16, 1974 and now abandoned.

BACKGROUND OF THE INVENTION

1. Field of the Invention

This invention relates generally to the field of compound identification and, more particularly, to a novel system having the capability to rapidly, automatically, and specifically identify and quantitate any one of a set of pre-selected compounds from unknown and impure samples. The present invention is described with respect to an embodiment incorporating a mass spectrometer.

2. Prior Art

The use of mass spectrometry for the indentification of compounds and determination of their molecular structure is well known in the art. In a mass spectrometer, a sample gas is partially ionized by electron impact or other means in an ion source. For each compound in the sample, a set of fragment ions are typically formed, each one having a particular mass to charge ratio, $m/e$, where $m$ is the mass of the ion in atomic mass units and $e$ is the charge of the ion determined by the number of electrons removed therefrom by the ionization. The mass to charge ratio, $m/e$, is usually referred to as "mass".

The ions are separated by electric, magnetic or combined fields (in a mass analyzer) into different species according to their respective masses. In the usual arrangement of the mass analyzer, ions of one mass at a time are transmitted to a suitable detector, typically an electron multiplier, for measurement and/or recording. Usually, the mass analyzer controls are manipulated so that the $m/e$ values are repeatedly and continuously swept over a selected mass range. A plot or tabulation of ion current or intensity vs $m/e$ is referred to as a mass spectrum and is the basic data output from a mass spectrometer. It should be understood that references to mass peaks made herein may apply to the amplitude of said ion intensity, the integral of ion intensity with respect to $m/e$, or any other quantitative measure of the presence of ions. If the mass separative power or resolution of the mass analyzer is such that integral values of $m/e$ can be separated but fractional values cannot, the technique is referred to as low resolution mass spectrometry.

One prior art example of mass analyzer control manipulation is disclosed by Krutz et al. (U.S. Pat. No. 3,642,420). Krutz et al. teaches the use of a computer to control the power supplies of a plurality of mass spectrometers. The Computer is programmed to intermittently vary the voltage of a mass spectrometer from one general area to another where known mass peaks corresponding to elements of interest are located. Once the computer has manipulated the power supply to the correct general area, it then increases and decreases the voltage within this area by very small increments so that a peak may be accurately defined. In this manner the mass peaks of the unknown compound may be located so that some independent means of identification may be used to determine the components of the unknown compound.

A second prior art example of mass analyzer control manipulation is disclosed by Laukien (U.S. Pat. No. 3,639,738). Laukien teaches the utilization of a computer to control the step-by-step scanning of a spectrum. In one embodiment spectral ranges of particular interest may be preselected so that such ranges may be repeatedly scanned. The existence or absence of a spectral line within the preselected ranges can be established through a form of statistical correlation. In a second embodiment, ranges of interest are determined by the signal amplitude present within the spectrum. Thus, the invention may be configured to repeatedly scan ranges wherein a signal exceeds a given threshold value.

Interpretation of the mass spectrum has two related but somewhat different objectives. Identification is the process of determining which (if any) compounds in a predetermined list or library are present in the sample, by means of a comparision of the sample spectra with previously recorded spectra of known pure compounds. In structure determination, part or all of the molecular structure of an unknown compound are deduced from the mass spectrum. This invention relates to the identification function of mass spectrometry (and the quantitation of the compounds identified).

The mass spectrum analysis for identification purposes may be performed manually or with the assistance of electronic analysis means. For a manual analysis, a skilled mass spectrometrist is normally required to study the data for features which suggest the possible identity of the compound sampled. Tables, computations, and application of rules of the formation of mass spectra are typically used. The final identification is usually made by a comparison of the selected sample spectrum with a published or measured spectrum for the compound identified.

Mass spectrum identification by electronic analysis means is typically accomplished by encoding or contracting the mass spectrum according to any one of a number of rules. Examples of some of the rules used include: (i) selection of $n$ most intense peaks; (ii) selection of one or two of the most intense peaks in each mass range of 14 amu; and (iii) binary encoding (indicating presence or absence only) of all peaks. The encoded spectrum is then compared with each of a number of similarly-encoded library spectra. Based on some criterion of similarity, the compound whose library spectrum most closely resembles that of the sample is identified as the compound which was sampled. Often more than one possible identification is provided, with the final identification being left to the operator based on comparisons of complete or encoded spectra.

An example of mass spectrum identification by electronic analysis is disclosed by Hargens, et al. (U.S. Pat. No. 3,027,086). Hargens et al. takes information from a direct reading spectrograph and produces a teletype record of the percent concentration of the component elements of the sample. Essentially, the Hargens et al. invention accepts signals from the spectrograph, which indicate the spectral line intensities, computes the percent concentration of the constituent elements, and then prints a record of the computation. Of course, of particular importance to such analysis is the separate and independent provision of electrical signals from the direct reading spectrograph. That is, in the Hargens et al. utilization of a spectrograph, the spectrograph provides signals which indicate the spectral line intensity ratio of a particular alloying element to a reference element. Then, the Hargens et al. device computes the percent concentration of the elements and provides a printed record of the product of the computation.

A second prior art example of electronic analysis of waveforms is disclosed by Watkins et al. (U.S. Pat. No. 3,614,408). Used in conjunction with chromatographs, the Watkins et al. device integrates the incoming signal between selected component peaks and valleys to provide a measure of particular band components. Thus, essential to the operation of this device is a "valley" sensor which indicates the absence of spectral peaks.

Use of mass spectrometry for identification presently requires purification of the sample by physical or chemical means. One or more abundant ions from an impurity could conceivably misdirect the identification of the compound sought. The purification may be accomplished before introduction of the smaple into the apparatus, or a separative device may be attached to the mass spectrometer. External means of sample purification include extraction (using control of pH and suitable solvents to preferentially dissolve the compound(s) of interest), distillation, recrystallization and thin layer chromatography. The separative device most commonly used with a mass spectrometer is a directly interfacing gas chromatograph (GC), providing the well known gas chromatograph/mass spectrometer (GC/MS) instrument. Recently, a liquid chromatograph has been used in conjunction with a mass spectrometer for separation of the sample.

In a gas chromatograph, a sample comprised of one or more compounds is injected by a syringe or valve into a heated chamber (the flash evaporator or injector) or directly into a chromatographic column. The sample is vaporized (if it is not already a gas) and transported through the column by a suitable inert carrier gas. The column is a glass or metal tube, usually packed with a powdered support material. The tube or the support material therein is coated with an organic liquid, called the stationary phase or liquid phase. The liquid phase has the property of absorbing and desorbing each of the constituent compounds in the sample at different rates, thereby causing a different rate of slowing of each compound as it passes through the column. As a result, the different constituents comprising the sample pass through the column at different rates and emerge therefrom at different times. Under fixed operating conditions (column type and temperature, flow rate, etc.) each compound has a characteristic, reproducible retention time, or delay from injection to elution at the column outlet. In this manner, a mixture is separated into its constituent compounds. Each compound then flows into the mass spectrometer for identification.

An interfacing device or separator is usually required between the outlet of the gas chromatograph and the inlet to the mass spectrometer, because the pressure at the column outlet is typically one atmosphere, while the mass spectrometer must operate in a vacuum of the order of $10^{-8}$ atmospheres. The separator transmits a reasonable fraction of the compounds of interest while excluding most of the carrier gas. Usually, a suitable non-selective detector is used to indicate GC peaks, that is, the elution of each of the constituent compounds. At least one mass spectrum is taken as each GC peak is detected.

The principal disadvantages of the instruments known in the prior art are as follows:

a. Where the mass spectrometer is not equipped with a separative device such as a gas or liquid chromatograph, lengthy, complex and tedious sample purification methods must be employed.

b. Where a separative device is used, the device itself imposes additional limitations. For example, only those constituent compounds of a sample which can be successfully separated by the separative device can be analyzed. Secondly, the operation of the separative device typically requires at least several minutes; thereby, it introduces a time delay. Moreover, the separative device increases the complexity of the instrumentation and the skill required to operate it.

c. Manual interpretation of mass spectra requires a great deal of time and skill.

d. Computing means for aiding the interpretation of mass spectrum used in the prior art, suffer from one or more of the following disadvantages: (i) a significant amount of operator intervention is necessary and, therefore, the interpretations are not fully automatic. In addition, a relatively high degree of operator skill is required. (ii) The computing means are typically used to make comparisons between a measured spectrum and library spectra, or characteristic peaks thereof. Such comparisons are made on the basis of an assumption that the spectrum measured is that of a pure sample. Thus, in order for the computing means to be effective, it requires purification of the sample (typically by means of a gas chromatograph). (iii) In making comparisons, the quantitative criteria of similarity typically applied by systems of the prior art do not reflect directly the probability that the identification is correct. (iv) The complexity of the comparison method requires the use of a high capability computer and/or temporary storage so that analysis can be completed after the data mseasurement is completed. Thus, the analysis cannot ordinarily be done in "real time", that is, as the measurement is being made. (v) Prior art computing means for identification of a compound from the mass spectrum typically fail to make use of some of the information available therein, including the absence or weakness of characteristic peaks and the differing significance of peaks as a function of their mass and intensity. (vi) The relatively long time required for the comparison process usually precludes an analysis of the plurality of spectra derived from mass measurement of the gas chromatograph effluent.

The present invention overcomes substantially all of the above-described limitations and shortcomings of the prior art instruments and methods. This invention enables the identification of any one of a number of a preselected "target" compounds in unknown mixtures of compounds with little or no sample purification. Thus, for one thing, it enables the elimination of a gas chromatograph or, at the least, a substantial reduction in its complexity. As a result, this invention provides a system which is less complex and less expensive than the corresponding systems of the prior art. In addition to the elimination or simplification of the gas chromatograph, the present invention further reduces the cost and complexity of compound identification by eliminating bulk data storage means. This is the result of its incorporation of means capable of real time analysis.

The present invention also enables greater specificity in the identification of compounds than that possible using the systems and methods of the prior art. This is due to the novel analysis means incorporated into the invention, means which (i) apply probabilistic techniques to the comparisons made; (ii) carry out exhaustive analysis of each spectrum measured; (iii) make use of negative information, e.g., the absence or weakness of characteristic peaks; and (iv) make use of calibration data "learned" from the invention itself. In addition, the analysis means of this invention can provide a confidence index, consistent for all target compounds, which quantitatively indicates the probability that the identification is correct.

The present invention enables automatic identification of compounds. This has the advantage of reducing to a minimum the skill and attention required of the operator. In addition, the invention enables rapid operation. For example, in applications where direct mass analysis gives satisfactory results, i.e., where chromatographic separation is not necessary, analysis of a sample can require as little as one second and is typically completed in 30 seconds, including data printout. Moreover, a greater variety of samples can be analyzed in situations where the chromatograph is eliminated than has heretofore been possible. Even in situations where some chromatographic separation is necessary, less analysis time is required than in the prior art because the degree of separation necessary to achieve satisfactory results is substantially reduced by the invention.

One further advantage of the present invention lies in its making possible the quantitation of identified compounds even when the target compound mass spectrum is largely obscured by other compounds in the mixture.

While some instruments disclosed by the prior art overcome some of the disadvantages described above, there has heretofore been no system which combines in one structure all of the features and advantages found in the present invention.

BRIEF SUMMARY OF THE INVENTION

The present invention is an automated mass spectrometric system comprising (i) a mass spectrometer, including its electronics and vacuum system; (ii) a sample inlet device; and (iii) electronic analysis means for analyzing the mass spectra obtained from samples; and (iv) electronic control means for controlling the operation of the mass spectrometer and certain of its operating parameters.

In a preferred embodiment of this invention, the mass spectrometer comprises an electron-impact ion source, quadrupole mass analyzer, electron multiplier detector and an ion pumped vacuum system. The sample inlet device is comprised of a flash evaporator and a membrane-type molecular separator. The control and analysis means may be implemented by a hard-wired, digital logic and control system or a programmable digital computer. In either case, appropriate input and output devices are required.

The invented system is arranged and operated so as to (i) measure and analyze the mass spectral data necessary to determine the presence or absence of one or more of a limited number of target compounds; (ii) measure the quantities of the compounds found; and (iii) display the results of the analysis rapidly and automatically. The system will operate properly with pure samples, mixtures, or partly separated mixtures. In addition, the invented system generates a confidence index which indicates the probability that the identification, if made, is correct.

The invented system handles mixtures or pure substances in the form of gases, liquids, or solids in solution in microgram quantities. A dual inlet arrangement allows gases to be introduced directly, or liquids to be injected into a flash vaporizer. In the case of liquid samples, the sample vapor is transported by a dry nitrogen stream. Trace amounts of material, even as low as 10 nanograms or less, can be identified in the sample.

Gas samples or vaporized liquid samples flow to an enrichment device, which preferentially extracts a large fraction of the organic compound contained in the sample stream from the permanent air gases. The sample-to-carrier enrichment ratio is very high, permitting routine sampling from atmospheric pressure environments. The enriched sample passes directly to an evacuated ionization region of the mass spectrometer where it is examined to acquire the spectral data necessary for the analysis, and then exhausted from the spectrometer. Operation of the mass spectrometer is controlled by the electronic control means, while analysis of the spectra taken is by the electronic analysis means, as more fully described below. Moreover, the control means is responsive to information generated by the analysis means, thereby providing closed loop control of the mass spectrometer as a function of the results of the analysis performed on the data theretofore acquired.

The electronic analysis means provide the unique capability of searching for and identifying the presence of specific target compounds in a sample by analyzing the mass spectral data output by the spectrometer in real time, despite the presence of a great many confusing mass peaks attributable to residual background and sample impurities.

The analysis means operates on the basis of a probabilistic matching of the mass spectral "fingerprint" of the sample with the characteristic mass spectral "fingerprint" of one or more of the target compounds. The characteristic mass spectral data of the target compounds are stored in a memory portion of the analysis means. In performing the matching function, the analysis means rejects spectral data which is distorted by the presence of constituents of the sample which are of no interest, that is, of contaminants in the non-pure sample.

Identification reliability is improved by taking into account the occurrence probabilities of the masses found to be present, the accuracy of the fit of the relative intensity pattern as compared with a stored reference pattern for the pure compound, and the compound concentration in the sample. In addition to using positive information, the matching procedure also makes use of negative information in the spectrum, basing the identification on the fact that particular peaks are absent, as well as that others are present, in the mass spectrum of the unknown sample.

The characteristic mass spectral "fingerprint" stored for each target compound is a contracted spectrum. Just as an experienced mass spectrometrist looks for characteristic peaks to determine if a particular compound is present, the present invention examines a predetermined set of masses most characteristic of the target compound, and compares the measured mass and their relative intensities with the stored reference spectrum. In the comparison, peaks which have excessive relative abundance are identified as contaminated and eliminated from the analysis.

Limiting the search to the most characteristic masses saves time which would otherwise be wasted measuring peaks which give no or less information as to the presence or absence of the target compound. To further reduce search time, only enough masses to assure reliable identification are used.

A confidence index is generated by the analysis means as a measure of the likelihood that the target compound is present. Even in non-random situations, as in discrimination among closely related compounds, the confidence index proves to be a useful indication of the confidence of mass spectral identification, which previously could be obtained only through the careful study of the mass spectral data by a trained mass spectroscopist. Presence of the target compound is indicated by a relatively high confidence index, depending on the quantity found and the degree of contamination. Other compounds, even when of similar molecular structure and present in high concentration, give relatively low values of the confidence index by this analysis method. Typically, reliable identification can be obtained over a concentration ratio of one hundred to one.

The quantity estimate is computed from the intensities of the uncontaminated peaks identified by the analysis means. In this manner, quantitation of a specific compound is possible even in a mixture which contains other compounds having many of the same masses. The response of the mass spectrometer is nearly linear over several decades. Thus, after a target compound is identified, its quantity is determined in units of weight (e.g., micrograms) by use of a stored scale factor. The scale factor is derived from the intensity measured for a known quantity of a pure sample of the target compound during an earlier calibration.

When the confidence index value indicates that the compound is probably absent, the quantity figure sets an independent upper bound on the target compound concentration. This is often very useful, as an extremely low quantity confirms the negative finding.

The present invention operates in at least four modes; i.e., start-up, calibration, identification, and a data system mode. In the start up mode, the invented system is placed in a condition for operation; e.g., operating temperatures and pressures and various parameters are established. In the calibration mode, the system automatically measures and records the reference mass spectral data for a given compound when an authentic sample is introduced. In addition, the background peak intensities of the system are measured in the absence of any sample material.

The identification mode is used to assay samples for the presence of one or more of the target compounds in either of two sub-modes. In a first such sub-mode, a confirmation mode, the system repeatedly attempts to match the spectrum of the injected sample with the characteristic spectrum of one pre-selected target compound. The sample is either continuously or sequentially injected into the sample inlet device and spectral masses measured repeatedly by the mass spectrometer. The analysis means generates a confidence index by application of the matching criteria and rules. If the confidence index is above a pre-established threshold for any target compound, a display is activated to indicate its presence. In addition, further information, such as the quantity of the target compound found, the magnitude of the confidence index, and/or the mass peak intensity may also be output by the system by conventional input/output devices. In the second identification sub-modes, a search mode, a probabilistic matching of the spectrum of the injected sample is attempted with each of a subset of the total number of target compounds whose spectral "fingerprints" are stored in the system.

In the data system mode, the invented system measures and displays the entire mass spectrum of an authentic sample, and ranks the mass peaks as to their significance for identification purposes by means of built-in probability tables. The spectral data so acquired may then be stored in the system, thereby adding that compound to the set of target compounds used for identifying unknown samples.

The present invention finds utility in a wide variety of applications, including (i) the forensic sciences, where it enables fast and accurate analysis of abused drugs in street sample mixtures; (ii) pharmacology, where its high sensitivity enables the measurement of drugs and metabolites in body fluids for clinical therapeutic study as well as urine screening; (iii) clinical toxicology, where its fast response time enables rapid identification, in a hospital environment, of drugs taken by comatose overdose patients, thereby facilitating their emergency treatment; (iv) industrial toxicology, where its automated capability enables 24-hour monitoring for multiple toxic compounds in a manufacturing plant. In addition, the invented system can also be utilized advantageously for the detection of air and water pollution, pesticides and explosives, even at relatively low concentrations.

Thus, the principal object of the present invention is to provide a means for rapid, automated, and specific identification and quantitation of compounds in unknown samples.

Another principal object of this invention is to provide the capability to make specific identification of mixtures of compounds (such as biological samples), as well as pure samples of compounds.

Another principal object of this invention is to provide, in mass spectrometric analysis, closed loop control of the data (mass peaks) to be acquired on the basis of analysis of data previously acquired, thereby saving time and reducing the amount of data storage required.

A further object of the present invention is to minimize the preparation of samples, reduce the complexity and cost of the system and reduce the levels of skill, experience, and training required of persons using the invented system.

A still further object of the invention is to provide a capability to process samples in either solid, liquid, or gaseous states.

Other objects, novel features, and advantages of the present invention will become apparent upon making reference to the following detailed description and the accompanying drawings. The description and the drawings will further disclose the characteristics of this invention, both as to its structure and its mode of operation. Although a preferred embodiment of the invention is described hereinbelow, and shown in the accompanying drawing, it is expressly understood that the descriptions and drawings thereof are for the purpose of illustration only and do not limit the scope of this invention.

BRIEF DESCRIPTION OF THE DRAWINGS

In the accompanying drawings, a preferred embodiment of the present invention is illustrated:

FIG. 1 is a general block diagram showing the five basic components of the invented system.

FIG. 2a is a cross-sectional view of a flash evaporator used in the sample inlet device of this invention.

FIG. 2b is a cross-sectional view of a separator used in the sample inlet device of this invention.

DETAILED DESCRIPTION OF THE INVENTION

Figure 3:
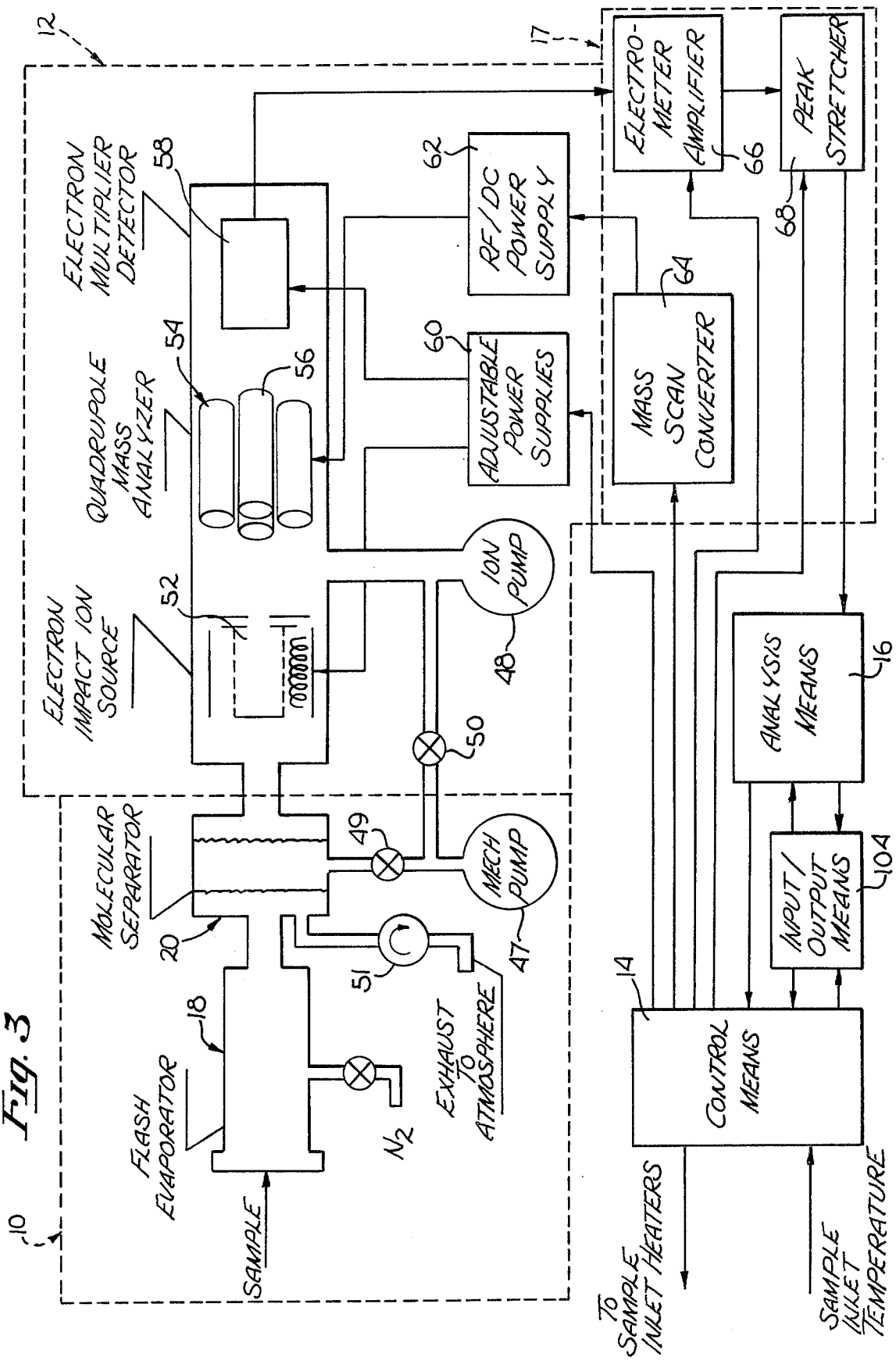
FIG. 3 is a more detailed functional block diagram of the invented system.

The present invention is comprised of the five basic components shown in FIG. 1, namely (i) a sample inlet device 10; (ii) a mass spectrometer 12; (iii) means 14 for controlling the operation of the mass spectrometer 12; (iv) means 16 for analyzing the mass spectra obtained from the samples; and (v) interfacing means 17 between the mass spectrometer 12 and the control and analysis means 14 and 16.

SAMPLE INLET DEVICE

The sample inlet device 10 is described with reference to FIGS. 2a and 2b. It is comprised of a flash evaporator 18 and a separator 20. The flash evaporator 20 is required for samples which are in either a liquid or solid state. It is comprised of a heated metal tube 22 having a glass insert 23, an injection port 24, an outlet port 26, and a carrier gas port 28. The injection port 24 is sealed with a septum 30, preferably made of a silicone rubber. The septum 30 is secured to the tube 22 by a septum nut 33. Liquid or dissolved or suspended solid samples are injected through the septum 30 with a syringe. The carrier gas port 28 is coupled by conventional means to a source of carrier gas under a slight pressure. A suitable carrier gas is nitrogen. A conventional heater (not shown) maintains the temperature of the flash evaporator 18 at a level suitable for evaporation of the sample.

In operation, volatile components of the sample are evaporated and swept by the gas carrier through the tube 22 and through a glass wool filter 32 disposed within the tube, wherein particulate matter in the sample is trapped. The outlet port 26 of the flash evaporator 18 is coupled to the separator 20.

If the sample is gaseous, the flash evaporator 18 is unnecessary. The flash evaporator 18 may be replaced with an inlet tube and the sample flowed directly into the separator 20. The separator 20 is comprised of a housing 36 having an inlet port 38, an outlet port 40, two thin polymer membranes 42a and 42b stretched across the interior of the housing 36 between the inlet port 38 and the outlet port 40; i.e., across the path of flow of the sample. An exhaust port 44 located in the housing 36 on the inlet side of the first membrane 42a enables the non-transmitted carrier gas and vaporized solvents to be vented to the atmosphere. A small suction pump 51 may be coupled to the exhaust port 44, and used to establish the flow of gaseous samples. Suction pump 51 is unnecessary for liquid or solid samples because the carrier gas provides the flow medium. A vacuum port 46 is provided in the housing between the membranes 42a and 42b. By means of a mechanical pump 47, coupled to the vacuum port 46 through valve 49, a pressure of about $10^{-2}$ torr or less is maintained in the interior space between the two membranes. The pressure in the mass spectrometer 12 is typically maintained at about $10^{-5}$ torr or less by an ion pump 48 (as shown in FIG. 3). Thus, a pressure differential is maintained across each membrane. In starting up the system, mechanical pump 47 is used to evacuate the mass spectrometer 12 through valve 50 (as shown in FIG. 3). The membrane temperatures are typically held between 150° C and 220° C, by a second conventional heater, the specific temperatures being a function of the target compound being sought.

Through preferential permeability the higher molecular weight sample vapors are transmitted through the membranes 42a and 42b much more efficiently than the carrier gas and solvents. Most of the latter are vented to the atmosphere or pumped from the region between the membranes, while an appreciable fraction of the sample vapor passes out of the outlet port 40 and enters the mass spectrometer 12. Sample enrichment by a factor of $10^6$ is possible and a large number of compounds are concentrated by a factor of $10^5$ or more.

Pressures, temperatures, and the carrier-gas or sample flow rate are parameters which are monitored and controlled by conventional means.

A number of other separators, known in the art, are suitable for use in the present invention in lieu of the separator 20 described above. Such other separators include effusion separators, jet orifice separators, and a single membrane separator like that disclosed in U.S. Pat. No. 3,751,880, granted to Michael Holm.

Solid samples are generally prepared by dissolving them in a suitable solvent. Aqueous or low-molecular weight solvents such as methanol, ethanol, acetone or ether are preferable. In complex or dilute mixtures, it is advantageous to use a suitable extraction procedure. Silylation, methylation or other standard derivatization methods may improve sensitivity and specificity.

Liquid samples may be introduced by continuous or discrete injection. If the concentration in the original matrix is too low, or if there is serious contamination of the sample, standard laboratory methods of extraction and concentration are used. For example, body fluids such as blood or urine are prepared for drug analysis by solvent extraction at an appropriate pH, or non-ionic resin column isolation. The invented system, while not requiring purification of the sample by means such as a gas chromatograph, is nevertheless adapted to operate with a gas chromatograph; thereby, users of the present invention have a choice between a direct analysis mode and a gas chromatograph/mass spectrometer (GC/MS) analysis mode. In the latter mode any suitable adapter known in the art enables the continuous real time analysis of the effluent from the gas chromatograph. The time related separation of the sample into its constituent compounds improves the specificity of identification when mixtures are involved, and the retention time data generated by the gas chromatograph is useful as an independent check on the identifications made.

MASS SPECTROMETER

A detailed description of the mass spectrometer 12 is now made with reference to the system block diagram shown in FIG. 3. As is well known in the art, a mass spectrometer is basically comprised of an ion source, a mass analyzer, and a detector. In a preferred embodiment of this invention, the ion source is an electron impact ion source 52, wherein the sample gas is partially ionized by a beam of electrons. The ions so formed are electrostatically removed from the source and formed into a beam which is projected through the mass analyzer to impinge on the detector.

A preferred mass analyzer is a quadrupole mass analyzer 54 comprised of two pairs of metal rods 56 which, when excited by the proper combination of radio frequency (rf) and dc voltages, produce electric fields which cause the trajectories of all ions, except those in a narrow range of mass to charge ($m/e$) ratio (referred to herein as the "mass position") to be unstable. Thus, only ions at a selected mass position are allowed to reach the detector at a given instant. All other ions are deflected into the mass analyzer rods 56 or walls and, thereby, are undetected at that instant.

A continuous channel electron multiplier 58 is utilized as a detector of the mass spectrometer 12. The ion current which reaches this detector 58 and impinges upon its surface is amplified through the phenomenon of secondary electron multiplication. Typically, the output of the detector is an electron current equal to as much as $10^6$ times the detected ion current.

The mass spectrometer 12 is provided with adjustable power supplies 60 for energizing the ion source filament and electrodes, and the electron multiplier detector 58. The adjustable power supplies 60 may be adjusted by the control means 14 or manually. The overall sensitivity of the invented system is established by adjusting the power supply voltage to electron multiplier detector 58. This adjustment is done by looking at the intensity of a known mass peak of a known sample, typically the carrier gas. Moreover, changes in the gain of detector 58 may be compensated for by adjusting power supplies 60. Mass spectrometer 12 is also provided with an rf/dc power supply 62 which produces rf and dc voltages to excite the quadrupole mass analyzer 54. The rf and dc voltages are determined by a mass control voltage which is an analog of the mass position, ($m/e$); i.e., the mass position is related to the mass control voltage by a substantially constant scale factor. Thus, any mass position may be selected by providing the corresponding mass control voltage to the rf/dc power supply 62.

A number of suitable mass spectrometers are available in the trade. Moreover, it should be understood that the present invention contemplates any type of low or high resolution mass spectrometer. For example, chemical ionization may be used instead of the electron impact ionizer 52; likewise, a magnetic sector analyzer instead of the quadrupole mass analyzer 54, and a discrete dynode electron multiplier or an ion collector instead of the continuous channel electron multiplier 58. In addition, any vacuum system design capable of maintaining the necessary vacuum and having adequate pumping speed may be used.

INTERFACING MEANS

The interfacing means 17 are comprised of (i) a mass scan converter 64; (ii) a gain-controllable electrometer amplifier 66; and (iii) a peak stretcher 68, interconnected as shown in FIG. 3.

a. MASS SCAN CONVERTER

Figure 4:
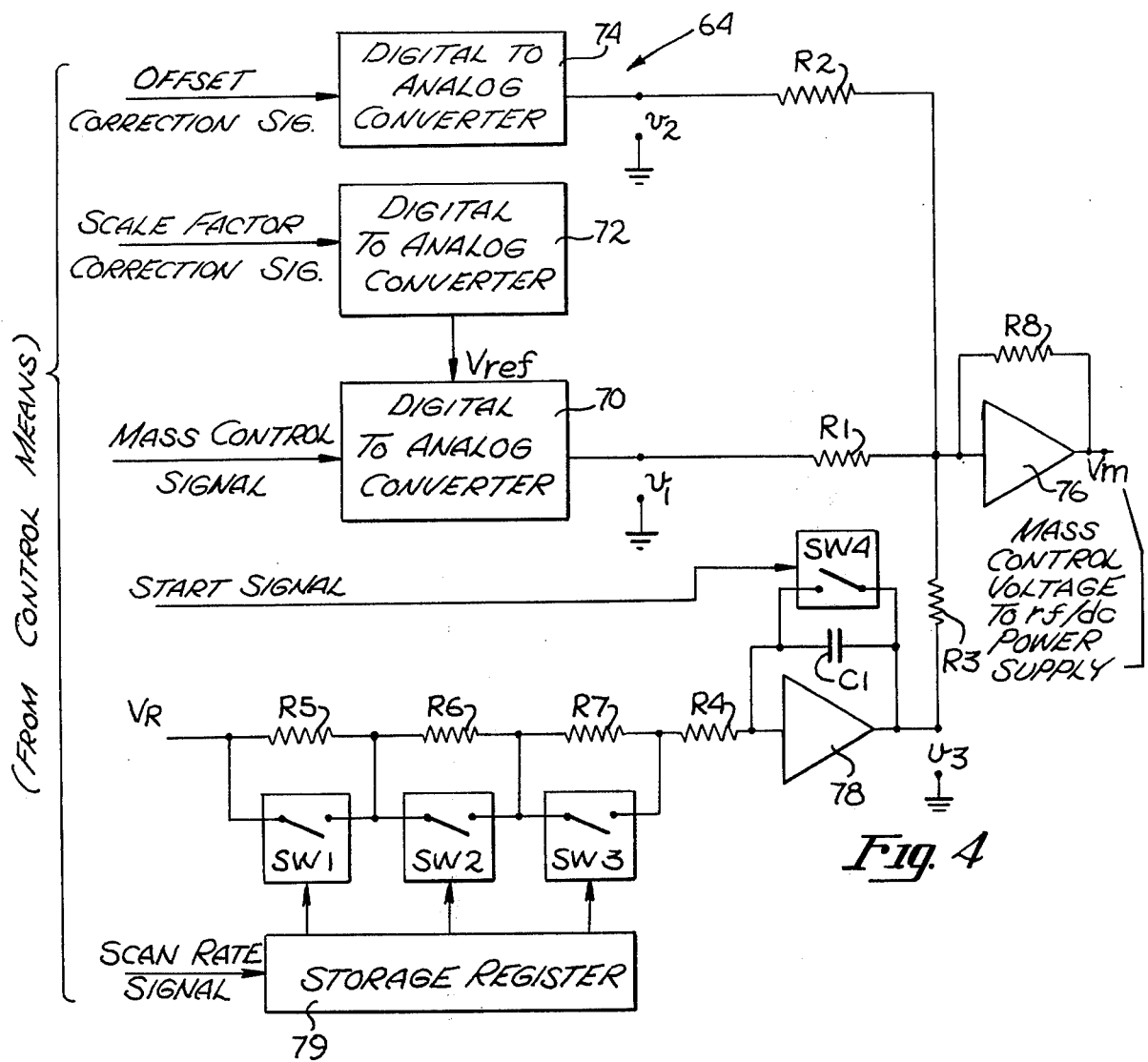
FIG. 4 is a schematic representation of the mass scan converter portion of the invented system.

The mass scan converter 64, shown schematically in FIG. 4, is disposed between the output of the control means 14 and the input control line of the rf/dc power supply 62. As indicated above, these rf and dc voltages control the scanning operation of the mass spectrometer 12 by means of its quadrupole mass analyzer 54. The control means 14 provides to the mass scan converter 64 a mass control signal, preferably in digital form, which is an analog of a particular mass position at which a mass peak is to be sought. The control means also provides a start signal to the mass scan converter 64. In response to the start signal, the mass scan converter 64 generates, as an output to the rf/dc power supply 62, the mass control voltage in the form of a ramp having an initial voltage approximately equal to that indicated by the mass control signal.

A typical mass control voltage generated by the mass scan converter 64 is 25 millivolts per atomic mass unit (referred to herein as the "mass control scale factor"). Thus, if the mass position to be scanned is 100 amu, the mass control voltage will be 2.5 volts. Because of the inherent uncertainty in establishing the precise mass position by an analog mass control voltage, a scan is required beginning at a mass position just below the selected mass position and ending just above it. This is accomplished by the ramp voltage. Such a scan ensures that the presence of a mass peak at a selected mass position will not go undetected because small, but cumulative, errors in the system cause a mass measurement to be made at a position slightly shifted from the selected mass position. Typically, the scan width is about ¾ amu centered on the selected mass position. The initial mass control voltage in the foregoing example would be about 10 millivolts below 2.5 volts.

It should also be understood that the mass control transfer function in an actual system is not perfectly linear over the entire mass range. Moreover, there may be a slight offset at zero volts and, in addition, this offset and the mass control scale factor may vary slightly with time and from unit to unit. In the preferred embodiment of the present invention the control means 14 generates scale factor and offset correction signals, preferably in digital form, on the basis of calibration data obtained by measuring the actual scan control voltage required to measure mass peaks at several precisely known mass positions. The scale factor and offset correction signals are stored in the mass scan converter 64 which correspondingly adjusts the initial mass control voltage. Remaining errors due to nonlinearity of the mass control transfer function are accommodated by the mass scan converter and peak stretcher designs described below.

With reference to FIG. 4, the mass scan converter 64 is now described in greater detail. First, second and third digital to analog (D/A) converters 70, 72, and 74 store and convert the mass control, scale factor correction and offset correction signals respectively, received from the control means 14. D/A converter 70 produces an output, $v_1$, which is proportional to the mass control signal. D/A converter 72 outputs an analog reference voltage, $v_{ref}$, to D/A converter 70. This reference voltage determines the ratio between voltage $v_1$ and the value of the mass control signal, which ratio is an analog of the mass control scale factor. Thus, control means 14 can compensate for the variations of the mass control scale factor by providing the appropriate value of the scale factor correction signal to D/A converter 72. D/A converter 74 produces an output voltage, $v_2$, which is proportional to the offset correction signal. Voltages $v_1$ and $v_2$ are electrically coupled to a conventional operational amplifier 76 through resistors $R_1$ and $R_2$ respectively. A feedback resistor $R_8$ is electrically coupled between the input and output of operational amplifier 76, thereby making it an adder of its input voltages, as is well known in the electronics art.

A second conventional operational amplifier 78 produces an output voltage, $v_3$, which is coupled to operational amplifier 76 through resistor $R_3$. A feedback capacitor $C_1$ is coupled between the input and output of operational amplifier 78, thereby making it an integrator of a constant dc voltage, $v_R$. Thus, voltage $v_3$ is a ramp voltage, equal to $V_R t / R_i C_1$ ), where $R_i$ is the input resistance of operational amplifier 78 and $t$ is time. The value of $R_i$, and therefore the slope of the ramp, or rate of the scan is a function of the states of conventional binary switches $SW_1$, $SW_2$, and $SW_3$ which, when closed, short out input resistors $R_5$, $R_6$, and $R_7$ respectively. The states of switches $SW_1$, $SW_2$, and $SW_3$ are controlled by the states of corresponding flip-flops in a storage register 79, wherein a digital "scan rate" signal, received from control means 14, is stored. Thus, $R_i$ can be as low as $R_4$, and as high as $R_4 + R_5 + R_6 + R_7$.

A conventional binary switch $SW_4$ is connected across feedback capacitor $C_1$. The state of switch $SW_4$ is determined by the start signal received from control means 14. When switch $SW_4$ is closed, capacitor $C_1$ is shorted out and $v_3$ equals zero. When switch $SW_4$ is opened, the ramp voltage $v_3$ appears as the integration of voltage $v_R$ begins.

The output voltage, $v_m$, of operational amplifier 76 is the mass control voltage which is electrically coupled to the rf/dc power supply 62. Since operational amplifier 76 functions as an adder, $$v_m = \left[ \frac{v_1}{R_1} + \frac{v_2}{R_2} + \frac{v_3}{R_3} \right] R_8$$

Thus, voltages $v_1$ and $v_2$ determine the dc level or pedestal of $v_m$ while $v_3$ provides the ramp portion thereof.

Binary switches $SW_1$, $SW_2$, $SW_3$, and $SW_4$ may be relays or transistor switches. Many suitable electronic switches are available in the trade.

b. ELECTROMETER AMPLIFIER

Figure 5:
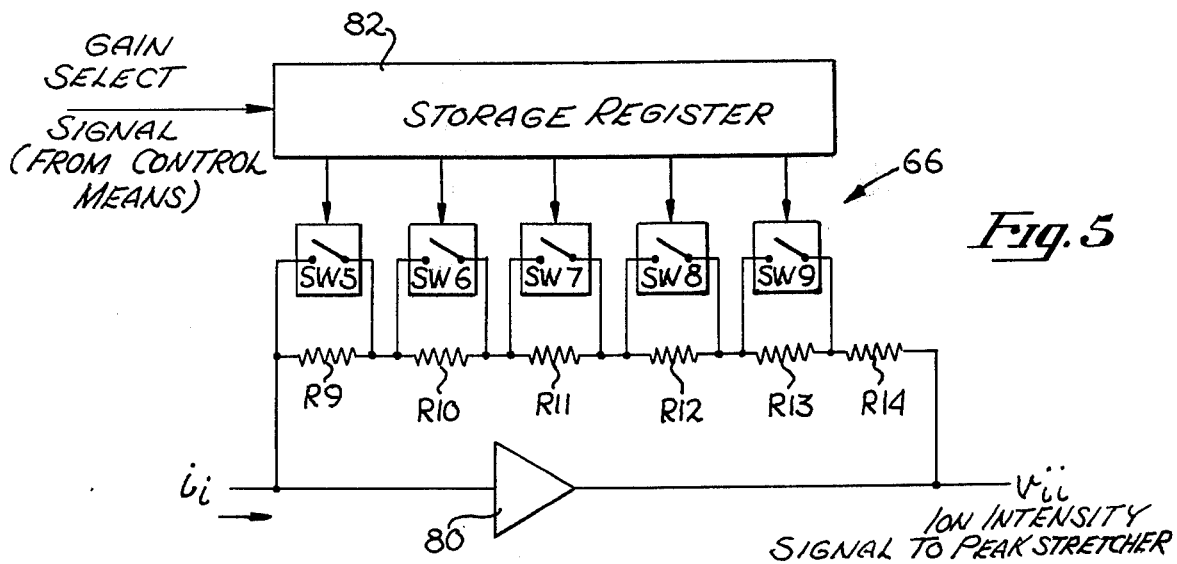
FIG. 5 is a schematic representation of the electrometer amplifier portion of the invented system.

The gain-controllable electrometer amplifier 66, shown schematically in FIG. 5, is disposed between the detector 58 of the mass spectrometer 12 and the peak stretcher 68. It converts the output current from the detector 58, representing an analog of the intensity of the ions at the mass position selected by control means 14, into a voltage analog thereof (referred to herein as the "ion intensity signal"). The electrometer amplifier 66 is adapted to having its voltage-to-current sensitivity or gain digitally set to one of a number of values, as required to amplify the ion current peaks to appropriate levels for measurement. In this preferred embodiment, any one of six gain settings for the electrometer may be selected by means of a "gain select" signal from the control means 14. However, manual control is also contemplated by this invention.

With reference to FIG. 5, the gain-controllable electrometer amplifier 66 is now described. It is comprised of a conventional operational amplifier 80 having resistors $R_9$, $R_{10}$, $R_{11}$, $R_{12}$, $R_{13}$, and $R_{14}$ electrically coupled between its input and output. Corresponding conventional, binary switches $SW_5$, $SW_6$, $SW_7$, $SW_8$, and $SW_9$ are coupled across resistors $R_9$, $R_{10}$, $R_{11}$, $R_{12}$, and $R_{13}$ respectively. When any switch is in its closed state, the corresponding resistor is shorted out. The states of switches $SW_5$, $SW_6$, $SW_7$, $SW_8$, and $SW_9$ are controlled by the states of corresponding flip-flops in a storage register 82, wherein a digital gain select signal, received from the control means 14, is stored. Thus, the feedback resistance across operational amplifier 80 can be any one of six values, depending upon the states of the switches $SW_5 - SW_9$. The voltage output of operational amplifier 80, $v_{ii}$, the ion intensity signal, equals the ion current $i_i$ multiplied by the magnitude of the feedback resistance.

c. PEAK STRETCHER

Figure 6:
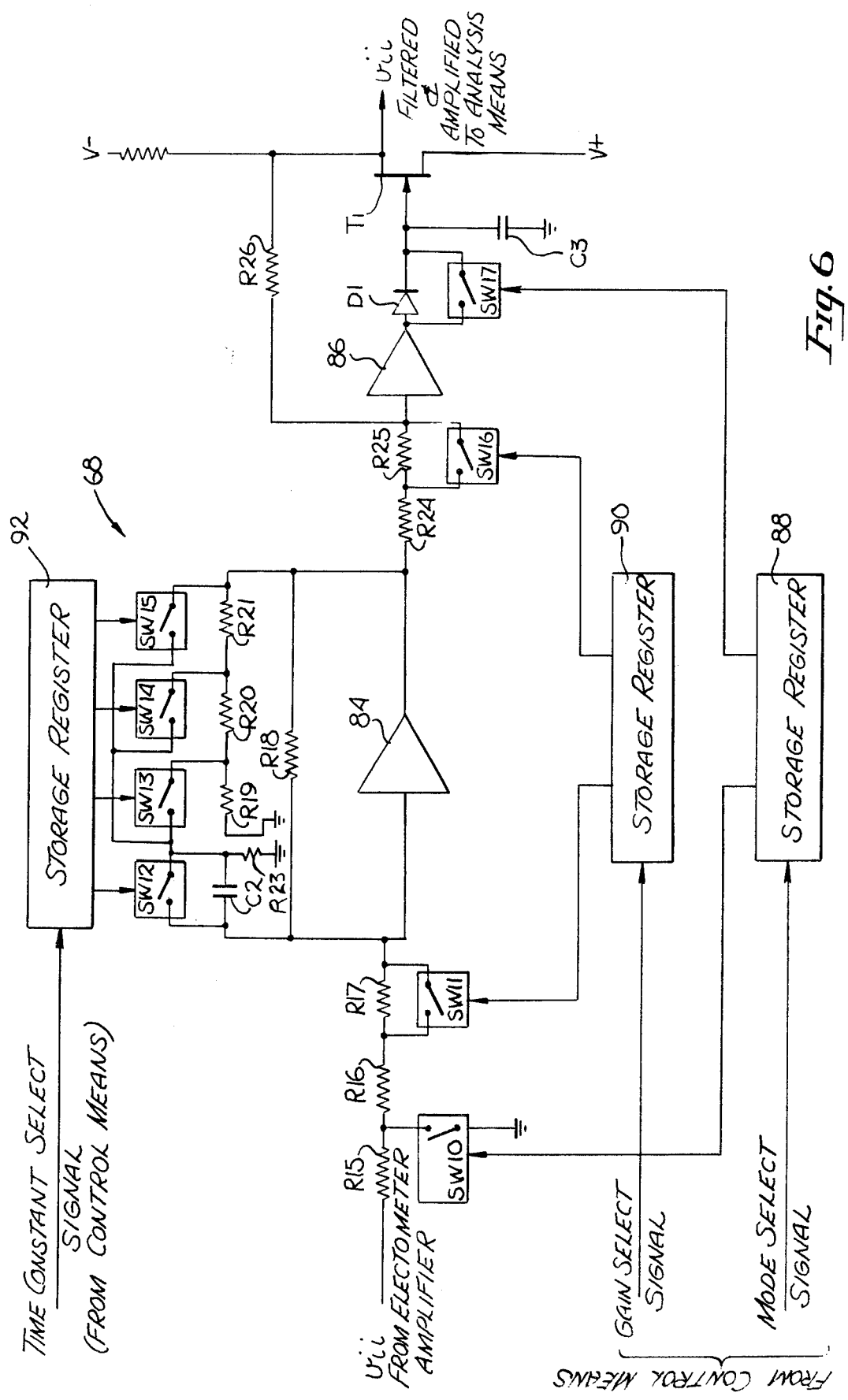
FIG. 6 is a schematic representation of the peak stretcher portion of the invented system.

The peak stretcher 68, shown schematically in FIG. 6, is disposed between the electrometer amplifier 66 and the analysis means 16. The peak stretcher processes the ion intensity signal which is output by the electrometer amplifier 66. The peak stretcher 68 has two principal operating modes, descriptively referred to as "hold" and "blank". In the hold mode, the ion intensity signal is filtered and amplified, and the maximum amplitude of the signal; i.e., the peak intensity during a mass scan, is held and presented to analysis means 16 by peak stretcher 68. In the blank mode, the input to the peak stretcher 68 is shorted, thereby preventing the ion intensity signal from reaching the analysis means 16. In addition, the previously stored signal is removed in preparation for the next scan.

In the preferred embodiment described herein, the peak stretcher 68 has four values of selectible voltage gain and four values of selectible filter time constant. Selection of the appropriate gain and filter time constant is by the control means 14, although manual selection is also contemplated by this invention.

With reference to FIG. 6, the peak stretcher 68 is now described. The ion intensity signal, $v_{ii}$, is input to a conventional operational amplifier 84 through input series resistors $R_{15}$, $R_{16}$, and $R_{17}$. Coupled between the input and output of operational amplifier 84 is a voltage resistor $R_{18}$. A capacitor $C_2$ can be connected to a resistive divider $R_{19}$, $R_{20}$, and $R_{21}$, via analog switches $SW_{13}$, $SW_{14}$, or $SW_{15}$. Conventional binary switch $SW_{10}$ is connected to one side of resistor $R_{15}$. When $SW_{10}$ is closed, $v_{ii}$ is shunted to ground through resistor $R_{15}$. This is the state of switch $SW_{10}$ when peak stretcher 68 is in its blank mode. Another switch, $SW_{11}$, is coupled across input resistor $R_{17}$. In its closed state, switch $SW_{11}$ shorts out resistor $R_{17}$, thereby affecting the gain of operational amplifier 84.

When switches $SW_{13}$, $SW_{14}$ and $SW_{15}$ are open and $SW_{12}$ is closed, resistor $R_{23}$ merely shunts the input of amplifier 84 — there is no filtering and the filter capacitor $C_2$ is discharged. With switch $SW_{12}$ open and $SW_{15}$ closed, the full filtering time constant $R_{18}C_2$ is effective.

Closing only $SW_{14}$ or $SW_{13}$ causes a feedback voltage derived from the $R_{21}$, $R_{20}$, $R_{19}$ divider to be applied to $C_2$, effectively multiplying $C_2$ by the attenuation of the divider factor, and thereby reducing the effective filter time constant of amplifier stage 84 without changing its gain.

The voltage at the output of operational amplifier 84 is electrically coupled to the input of a second operational, amplifier 86 through series input resistors $R_{24}$ and $R_{25}$. Coupled between the input and output of operational amplifier 86, through field effect (FET) transistor $T_1$, is a feedback resistor $R_{26}$. The gate of transistor $T_1$ is electrically coupled to the output of operational amplifier 86 through low-leakage diode $D_1$ or switch $SW_{17}$, when closed. A capacitor $C_3$ is connected between the output of operational amplifier 86 and circuit ground; thus, it charges to the output voltage thereof. The output of peak stretcher 68 is taken at the source of transistor $T_1$. When switch $SW_{17}$ is closed, the output of the peak stretcher 68 is the filtered and amplified ion intensity signal $v_{ii}$. When $SW_{17}$ is open, capacitor $C_3$ cannot discharge through low leakage diode $D_1$ or the gate of FET $T_1$; therefore, it will retain the most positive voltage applied to the gate of $T_1$. Through the feedback action of resistor $R_{26}$, the corresponding most positive value of the $v_{ii}$ will be retained at the output of peak stretcher 68.

A conventional binary switch $SW_{16}$ is coupled across input resistor $R_{25}$. In its closed state, switch $SW_{16}$ shorts out resistor $R_{25}$, thereby affecting the gain of operational amplifier 86.

The states of switches $SW_{10}$ and $SW_{17}$, the mode switches, are controlled by the state of corresponding flip-flops in a storage register 88, wherein a digital "mode select" signal, received from control means 14, is stored. The states of switches $SW_{11}$ and $SW_{16}$, the gain control switches, are controlled by the states of corresponding flip-flops in a register 90, wherein a digital "gain select" signal from control means 14 is stored. Four values of gain are possible based upon the four combinations of the states of switches $SW_{11}$ and $SW_{16}$. The states of switches $SW_{12} - SW_{15}$, the time constant (and filtering) select switches, are controlled by the states of corresponding flip-flops in a storage register 92, wherein a digital "time constant select" signal from control means 14 is stored.

CONTROL MEANS

Figure 7:
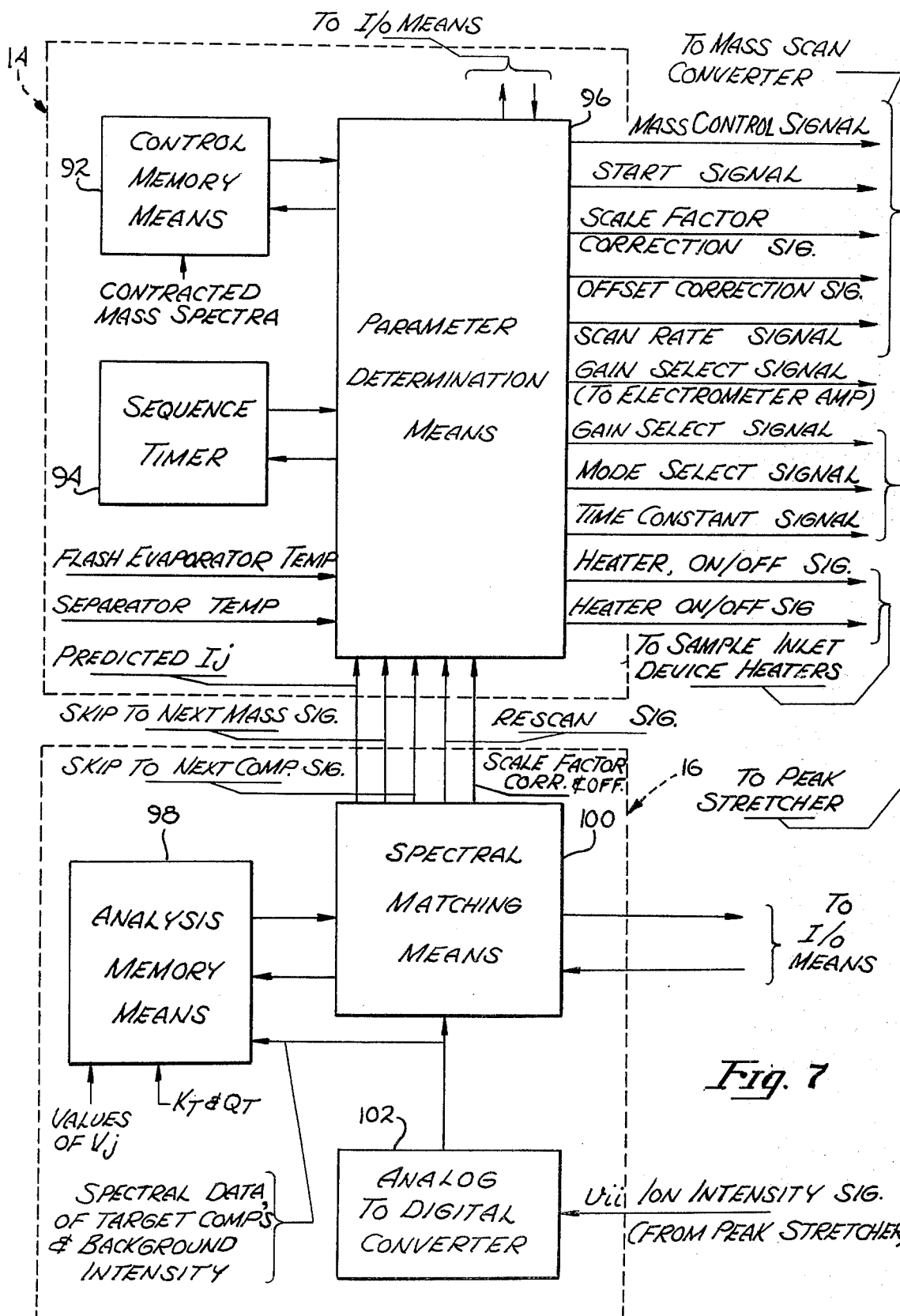
FIG. 7 is a functional block diagram of the control means and analysis means of the invented system.

The control means 14, described with reference to FIG. 7 controls (i) the mass scanning of the sample in the mass spectrometer 12; and (ii) certain operating parameters of the system. The control means 14 is comprised of a memory means 92, a sequence timer 94, and a parameter determination means 96, all of which can be implemented by a programmable digital computer utilizing known techniques of computer programming or a hard-wired, logic and control system utilizing known techniques of logic design and available integrated circuit logic components.

One example of a programmable digital computer which could be used to implement the control means 14 is the Intel Corporation's MCS-8 microcomputer system. This computer system comprises the 8008central processor unit along with a combination of random access memories, read only memories and shift registers. As indicated in the *Intel Data Catalog* of February, 1973, at pages 6–19, the MCS-8 system will provide complete computing and control functions for measuring systems and process control systems. Programming of the MCS-8 system is facilitated by Intel Corporation's *MCS-8 Assembly Language Programming Manual*. This manual published in November, 1973, would aid one who sought to implement the control means 14 through the use of the MCS-8 system. As the manual indicates at page 1-1, a high degree of skill in computer programming is not required, since the manual assumes that the reader is completely unfamiliar with programmning concepts. Thus, given the necessary control functions as disclosed herein, the Intel MCS-8 microcomputer system may be readily programmed to provide the control means 14. A system marketed by Universal Monitor Corporation and commercially available in the early part of 1974 employed the Intel 8008 central processor unit in a design substantially similar to the MCS-8 microcomputer to perform the function of the control means 14.

Figure 8:
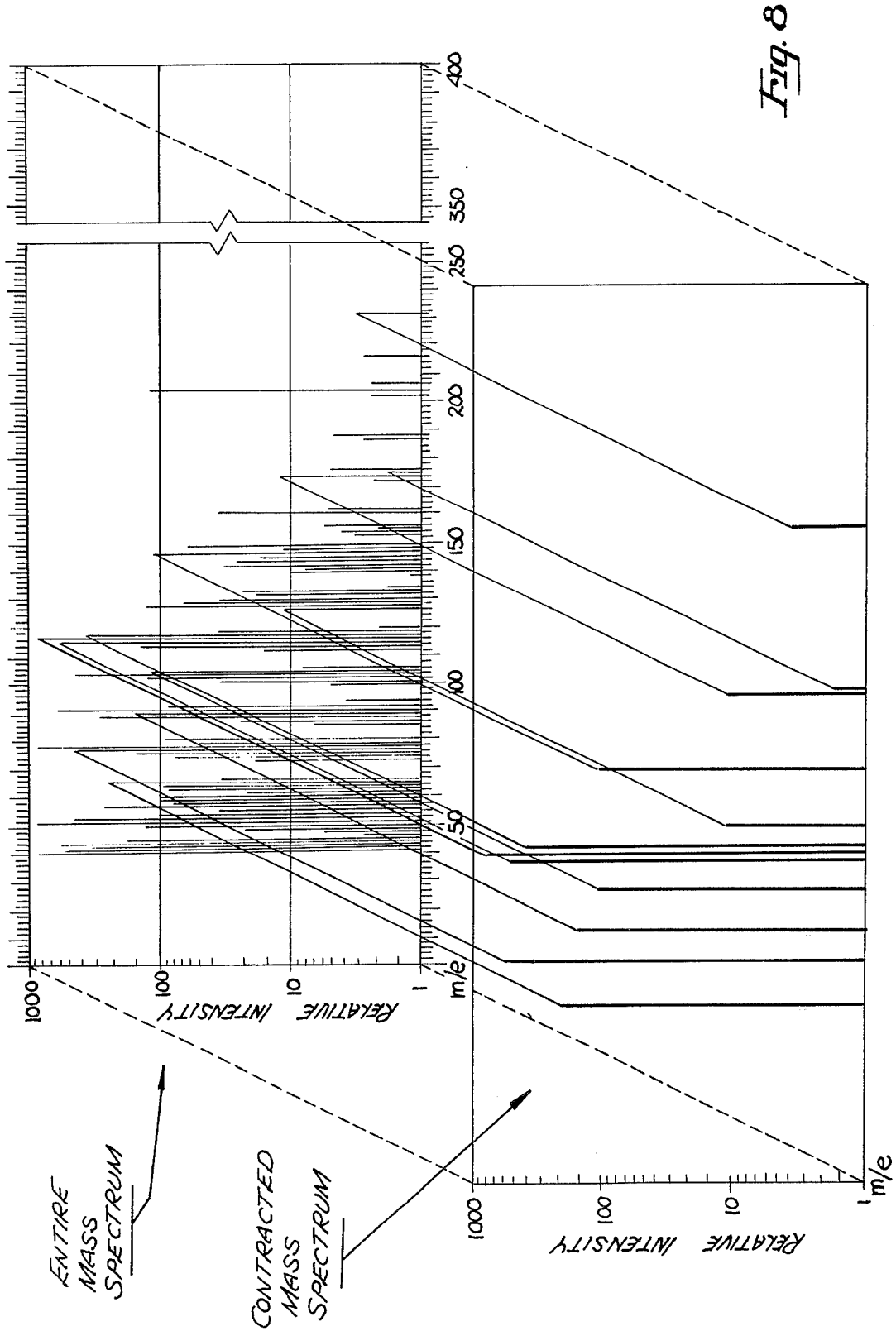
FIG. 8 shows the relationship between a complete mass spectrum of a particular compound and its contracted mass spectrum.

Each target compound selected for identification by the invented system has a unique mass spectrum. Each such mass spectrum is comprised of mass peaks located at various mass positions. A particular subset of all the masses can be predetermined as being especially characteristic of each target compound. This set of masses is called the "contracted mass spectrum". The relationship between the complete mass spectrum of a hypothetical target compound and it contracted mass spectrum is illustrated in FIG. 8. In the background is shown a full mass spectrum of a particular compound. In the foreground is the selected subset of mass peaks comprising the contracted mass spectrum of the compound. The criteria for selecting the contracted mass spectrum is discussed hereinbelow.

The masses for the contracted mass spectrum, of a given target compound spectrum, are selected and ranked according to how characteristic they are of that particular compound. This "characteristicness" is a function of (i) how unusual, on a probabilistic basis, the very existence of a peak at that mass position is, and (ii) the magnitude of the intensity of the peak (referred to as "abundance"). The contracted mass spectrum for each target compound, i.e., the mass position of each peak thereof, is stored in the control memory means 92. In any event, for each target compound being sought in a sample, the parameter determination means 96 initiates a mass scan sweep about each mass position for a predetermined scan period and width. The mass position relating to the most characteristic mass peak for the target compound sought is the first one selected by the parameter determination means 96. After the sample is analyzed for the first and most characteristic peak, the mass position relating to the next most characteristic peak is selected and a scan about it initiated. The parameter determination means 96 continues operating in this manner until all of the mass peaks in the pre-stored contracted spectrum of the particular target compound have been scanned, unless the sequence is modified by the analysis means 16, as more fully described below.

Figure 9:
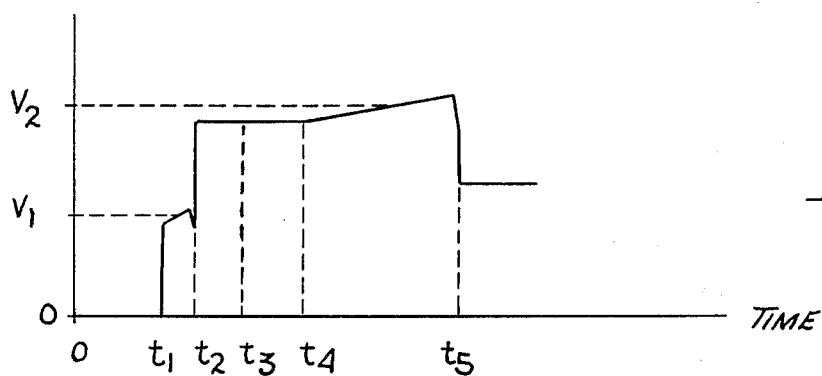
FIG. 9 shows the voltage waveform at the output of the mass scan converter.

The waveform of the mass control voltage output of the mass scan converter 64 is shown in FIG. 9. The waveform relates to scan about mass control voltages $V_1$ and $V_2$, corresponding to two mass positions at about $40V_1$ amu and $40V_2$ amu respectively (based upon a mass control scale factor of 25 millivolts per atomic mass unit). The start time for the first scan is $t_1$; the scan ends at $t_2$. The scan period is a variable determined by the parameter determination means 96. At about time $t_2$, a mass step occurs to a voltage corresponding to a mass position just below the second selected mass position, $40V_2$ amu. The second scan starts at $t_4$ and ends at $t_5$.

Figure 10:
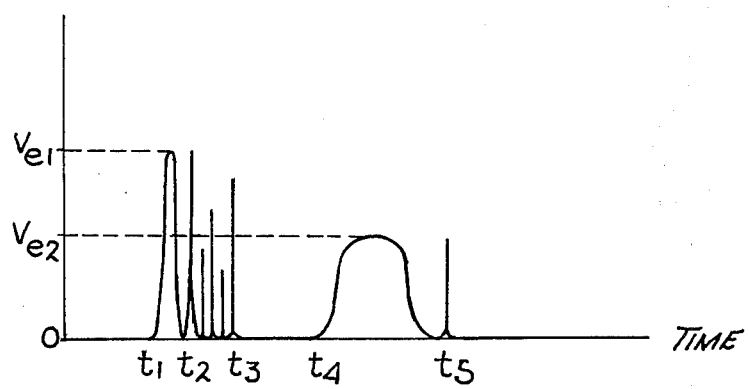
FIG. 10 shows the voltage waveform at the output of the electrometer amplifier.

The inter-scan interval $(t_4 - t_2)$ is comprised of two delays. The first delay, $(t_3 - t_2)$, allows the rf/dc power supply 62 to respond to the step in the mass control voltage. The second delay, $(t_4 - t_3)$, allows the electrometer amplifier 66 to recover from the spurious ion intensity signals which occur between $t_3$ and $t_2$ as a result of the mass sweep of the mass spectrometer 12. (These spurious signals are shown in FIG. 10, which shows the waveform at the output of the electrometer amplifier 66 in the same time frame as that of the mass scan converter output.) Even if the same mass position is being rescanned, an interscan interval is still required although the first delay would be relatively small. The first delay is a function of the magnitude of the mass step. The second delay is a function of (i) the previous time constant setting of the filter in the peak stretcher 68, which filter must be discharged before the next scan; (ii) the recovery time of the electrometer 66 after responding to the spurious ion intensity signals; and (iii) any changes in the settings of the gain of electrometer amplifier 66 and/or the gain and filter time constant of peak stretcher 68, required for the next measurement. The delays are determined by the parameter determination means 96 and clocked out by the sequence timer 72.

With reference to FIG. 10, the maximum values of the electrometer output voltage, $Ve_1$ and $Ve_2$, occur during the first and second mass scans respectively; i.e., during scan periods $(t_2 - t_1)$ and $(t_4 - t_3)$, representing the ion intensities at the selected mass positions. However, spurious signals also occur at the mass step times $t_2$ and $t_5$. These spurious signals are suppressed by placing the peak stretcher 68 in its blank mode for periods covering the times $t_2$ and $t_5$. This is accomplished by the parameter determination means 96 issuing a mode select signal to the peak stretcher 68 at these times.

Figure 11:
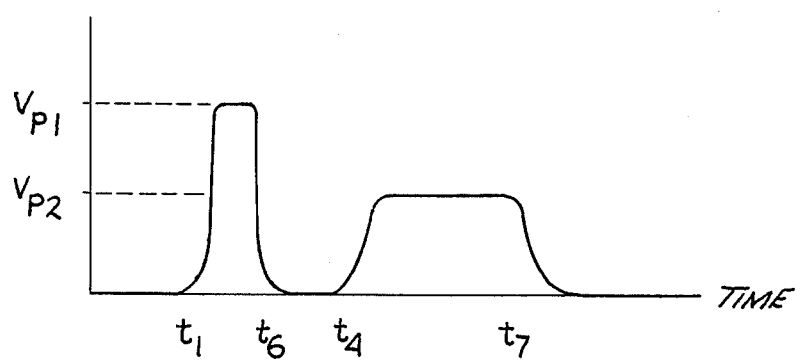
FIG. 11 shows the voltage waveform at the output of the peak stretcher.

The corresponding waveform at the output of the peak stretcher 68 is shown in FIG. 11. At scan start times $t_1$ and $t_4$, the parameter determination means 96 places the peak stretcher in its hold mode. In this mode, the maximum values of the electrometer amplifier output during each scan, after filtering and amplification, are held at the peak stretcher output for digitization and storage by the analysis means 16. The peak stretcher voltages $Vp_1$ and $Vp_2$ shown in FIG. 11 are proportional to the intensities of the two ion peaks at the two selected mass positions respectively. After the peak values are stored in the memory portion of the analysis means 16, the peak stretcher 68 is reset, to prepare for the next scan. This is accomplished by the parameter determination means 96 issuing an appropriate mode select signal to the peak stretcher 68 at times $t_6$ and $t_7$ to place it in its blank mode.

The sensitivity of the invented system is adjustable by selection of the gain of the electrometer amplifier 66 and/or the gain of the peak stretcher 68. The sensitivity must be adjusted so that the peak intensity measured is "on scale", i.e., neither clipped by saturation nor so low as to be obscured by noise. The scan rate and the filter time constant of the peak stretcher 68 are interrelated functions of the sensitivity setting of the system. When the sensitivity of the system is reduced, there is a need for greater filtering by the peak stretcher 68 in order to enhance the signal-to-noise ratio. Accordingly, for each sensitivity setting, the parameter determination means 96 provides a time constant select signal to the peak stretcher 68, so as to select the appropriate filtering required for that sensitivity setting. The amount of filtering, in turn, determines the scan period inasmuch as the frequency response of the filter must be compatible with the frequency content of the ion intensity signal. Thus, as the filtering is increased to enhance the signal-to-noise ratio, the scan rate is correspondingly decreased by the parameter determination means 74 so that the filter can pass the ion intensity signal. The interrelationships between spectrometer sensitivity, i.e., electrometer and peak stretcher gain, filter time constant and scan rate, may be derived analytically and/or empirically. These relationships are stored in the control memory means 92 and utilized by the parameter determination means 96 to generate the appropriate parameter select signals. These signals are provided, at the appropriate times, to the mass scan converter 64, the electrometer amplifier 66 and the peak stretcher 68.

The parameter determination means 96 also receives the temperatures of flash evaporator 18 and of the separator 20. These temperatures are converted to voltages by appropriate temperature transducers and converted to digital form for presentation to the parameter determination means 96. The parameter determination means 96 typically controls the on-off cycles of the heaters associated with flash evaporator 18 and separator 20, as required to maintain the desired temperatures.

CONTRACTED SPECTRUM

Before describing the analysis means 16 and its operation upon the ion intensity signals output by the peak stretcher 68, the criteria used to contract the mass spectrum of each target compound is described.

It is well known that the existence of mass peaks in mass spectra are much less common at certain mass positions, especially those of higher atomic mass units. Thus, if a target compound has large peaks at mass positions $(m/e)$ 43 and 243, most mass spectrometrists, for identification, would look first in the unknown spectrum for the presence of the peak at mass position 243, knowing it to be a much more selective criterion if the sample could be any one of a relatively random selection of compounds.

In order to define this "uniqueness" as a more quantitative "U" value, it is necessary first to select a particular universe of all compounds of interest and to obtain their known mass spectra from available reference sources such as, for example, the 17,124 compounds found in the "Eight Peak Index of Mass Spectra" published by the Mass Spectrometry Data Centre, AWRE, Aldermaston, Berkshire, England, 1970. The target compounds, of course, are a subset of the compounds in the selected universe. The U values will only be applicable to spectra measured under conditions comparable to those employed to measure the spectra of the compounds in the universe of interest.

Abundance is defined as the ratio of the intensity of a mass peak, at a given mass position, to a base intensity, the latter being the maximum normalized intensity in the entire spectrum. The U value is based on the probability that, at a particular mass position, a spectrum taken at random would have a mass peak with an abundance greater than 50%. More specifically, U is defined, for each mass position, to be the logarithm to the base 2 of the number of randomly selected mass spectra (taken from the universe of interest) which would have to be examined to find one having a peak at that mass of greater than 50% abundance $$U_j = \log_2 N_j \qquad 1.$$

Where $U_j$ is the U value at the $j^{th}$ mass position and $N_j$ is the number of randomly selected spectra which would have to be examined as described above. It, therefore, follows that:

$$p(j) = 1/N_j \qquad 2.$$

where $p(j)$ is the probability that, at the $j^{th}$ mass position, a mass peak of 50% abundance exists; i.e., that any given spectrum in the universe of interest will satisfy the foregoing condition. Thus, since:

$$N_j = 2^{U_j} \qquad 3.$$

$$p(j) = 1/2^{U_j} \qquad 4.$$

For each mass position, the value of $N_j$ can be determined from examination of the library of spectral data for the universe of interest, and the $U_j$ values derived from $N_j$. For simplification, the $U_j$ values are rounded to the nearest integer value.

It has been observed that the uniqueness of a particular mass peak is a function of its abundance level. For example, in the Aldermaston universe of compounds, the data shows that approximately one in 32 spectra (U=5) have a mass peak of greater than 50% abundance at mass position 45 amu. However, at that mass position, nearly half the spectra have a peak of greater than 1% abundance. Thus, at any mass position, the number of randomly selected mass spectra which would have to be examined to find one having a mass peak of a particular abundance generally decreases as the abundance level decreases. Thus, the probability function can be expressed as $$p(j) = 1/2^{(U_j - A_j)} \qquad 5.$$

where $A_j$ is an abundance term reflecting the effect of the abundance level of the peak on the probability of occurrence. At abundance levels between 50% and 100%, $A_j = 0$. The values of $A_j$ can be determined from examination of the library of spectral data for the universe of interest. A large sampling of spectral data shows that, for most masses, the following Table I gives a satisfactory approximation of the abundance factor A necessary to adjust the probability of occurrence as a function of the mass peak abundance. The abundance factor A is substantially independent of the mass position of the peak.

Table 1

| Abundance Range | A |
|---|---|
| 50 – 100% | 0 |
| 19 – 50% | 1 |
| 7.1 – 19% | 2 |
| 2.7 – 7.1% | 3 |
| 1.0 – 2.7% | 4 |
| 0.38 – 1.0% | 5 |

The known spectral data for each target compound is examined and the value of $U_j - A_j$ (referred to as $V_j$ for convenience) is determined for each mass peak thereof. For example, if the target compound is known to have a mass peak of 30% abundance at mass position 45, $U_{45} = 5$ (in the Aldermaston universe of compounds). From the above table $A_{45} = 1$. Thus, $V_{45} = 4$. The subset of all peaks in the mass spectrum of the target compound which have the highest values of V are the most unique and, therefore, are selected to comprise the contracted mass spectrum of that compound. Ordinarily, the subset of peaks is chosen in decreasing order of $V_j$. However, any available supplementary information, such as the fact that certain peaks may relate to key structural features of the molecule, may be used in the selection process. In addition, only those peaks which can be reliably measured when a threshold quantity of the target compound is introduced should be selected. The number of peaks selected is a function of the confidence level desired for an identification.

ANALYSIS MEANS

Analysis means 16 is comprised of analysis memory means 98, spectral matching means 100, and an analog to digital (A/D) converter 102, all of which can be implemented by a programmable digital computer utilizing known techniques of computer programming or by a hard-wired, logic and control system utilizing known techniques of logic design and available integrated circuit logic components. In a manner similar to the implementation of the control means 14, one example of implementation of analysis means 16 is the Intel Corporation's MCS-8 microcomputer system. A system marketed by Universal Monitor Corporation and commercially available in the early part of 1974 employed an Intel 8008 central processor unit in a design substantially similar to the MCS-8 microcomputer to perform the function of the analysis means. Thus, by combining the MCS-8 with the system elements described herein and programming in accordance with the explanation and mathematics described herein, the MCS-8 system may be readily configured to provide analysis means 16.

The primary function of analysis means 16 is to analyze the measured spectral data of a sample for the presence of one or more of the target compounds. The contracted mass spectrum for each target compound, i.e., the mass position and relative intensity of each peak thereof, is stored in the analysis memory means 98. The measured spectral data of a sample is obtained at each mass position of each target compound sought as described hereinabove. The magnitude of the ion intensity signal output by peak stretcher 68 to analysis means 16 is, of course, the value of the mass peak at that mass position. The ion intensity signal is first converted to digital form by A/D converter 102 and then fed to spectral matching means 100 and stored in analysis memory means 98.

The first mass peak in the sequence is measured at an arbitrary and predetermined system sensitivity (determined by the gain of the electrometer amplifier 66 and peak stretcher 68). The scan rate and filter time constant are set by parameter determination means 96 to be appropriate for that sensitivity. If, after the first scan, the ion intensity of the first peak is too large or small for accurate measurement, the spectral matching means 100 outputs a rescan signal to the parameter determination means 96 indicating that the scan should be repeated at a higher or lower sensitivity as the case may be. The parameter determination means 96 responds by adjusting the gain of the electrometer amplifier 66 and/or that of peak stretcher 68 upward or downward as appropriate and the same mass position is rescanned. When the intensity of the first mass has been established, the maximum quantity of the target compound present is estimated from the known response sensitivity of the system to quantities of that compound. Based on the estimated quantity of the target compound which appears to be in the sample, and the relative intensity pattern of the target compound's contracted mass spectrum stored in analysis memory means 98, the intensity of the next mass to be sought in the contracted mass spectrum of target compound is predicted. The predicted intensity of the next mass peak in the sequence is output from spectral matching means 100 to parameter determination means 96. The latter, in response thereto, adjusts the system sensitivity for the next mass peak and the mass position thereof is scanned.

The value of the second mass peak measured is compared with the predicted value. If it exceeds the predicted value by more than a predetermined tolerance, the mass peak is identified as contaminated, that is, consisting of ions produced by at least one compound other than the target compound, as well as (possibly) the target compound. If, on the other hand, the measured intensity of the second mass peak is too small to measure accurately, the spectral matching means 100 outputs a rescan signal indicating that the scan should be repeated at a higher sensitivity. The sensitivity is increased appropriately and the mass position is rescanned. If the accurately measured intensity of the second mass peak is smaller than the predicted value by more than a predetermined tolerance, the estimated maximum amount of the target compound present is reduced based upon the known sensitivity response of the system to quantities of the target compound. In such an event the intensity of the previous (first) mass peak is predicted on the basis of the known relative intensity pattern of the target compound's contracted mass spectrum. The predicted intensity of the previous mass peak is then compared to the previously measured value thereof. If the previous mass peak exceeds the predicted intensity by more than a predetermined tolerance, then the previous peak is identified as "contaminated".

The above-described sequence is continued until the mass peaks at each of the mass positions in the contracted mass positions in the contracted mass spectrum have been measured. During and/or after the measurements described, a confidence index relating to the likelihood that the target compound is present, and an estimate of the quantity of the target compound which may be present, are determined from the mass peaks found to be uncontaminated. This is described more fully below.

For greater accuracy, the intensities of all mass peaks measured (including calibration intensities) are corrected by subtracting from the measured intensities the previously measured background intensities at all mass positions to be scanned for identification purpose. The background intensities are measured under conditions which are identical to those under which the sample identification is to be made, except that the sample is absent. Such background data is stored in analysis memory means 98.

In the event that a mass peak intensity at a particular mass position is predicted by spectral matching means 100 to be below the background intensity at that mass position, spectral matching means 100 issues a "skip to next mass" signal to parameter determination means 96. The latter responds by initiating a mass step at the appropriate time. The reason for skipping a measurement in view of such a prediction is as follows. If the prediction is correct or too high, the intensity can't be measured since it is in the "noise" of the system. If the prediction is too low, i.e., if the intensity of the peak were measured and it were higher than predicted (and measurable), it would nevertheless be identified as "contaminated" (since it would be greater than the predicted value) and would, therefore, contribute nothing to the confidence of the identification.

CONFIDENCE INDEX

The probability that the mass spectral data examined for a sample is due to the compound sought is determined in the form of a confidence index, K. The calculation of K involves a number of assumptions and approximations. Within these limitations, the probability that the mass spectral data measured could arise from a compound selected at random from the universe of compounds of interest is $\frac{1}{2}^K$. Thus, K is the logarithm to the base 2 of the probability of a random occurrence of the observed data.

In analyzing the unknown sample spectrum for the presence of a target compound, $K_j$ values are determined sequentially by spectral matching means 100 for each of the selected peaks sought. It is assumed that the various statistical contributions to the probability are independent, so that the overall probability is the product of the probabilities for each contribution. Therefore, K is a linear combination of the corresponding logarithms for uncontaminated peaks. Thus, $$K = \Sigma K_j = \Sigma(V_j + W_j - D_j),$$

where $V_j$ is the logarithm of the probability that a mass peak of a particular abundance will occur, at the jth mass position, as discussed above; $W_j$ is a window tolerance factor, reflecting the degree to which the matching of measured peaks to known peaks of the target compound occurs; and $D_j$ is a dilution factor based upon the amount of the target compound found relative to the quantity of sample introduced.

One requirement for the identification of the target compound in the unknown mixture is that the relative abundances of the peaks in the unknown spectrum must be consistent with those of the corresponding peaks in the contracted spectrum of the target compound. The probability that the required abundance has occurred instead by chance will depend on the expected degree of matching of these abundances. This, in turn, is a function of the tolerance to which matching is sought; i.e., the "window tolerance".

The range of abundance values is a function of the dynamic range of the system. Whatever the range of abundance values, it may be arbitrarily divided into a number of windows as a function of the tolerance of matching. Thus, for example, if the abundance range of the system is from 0.5% to 100%, there are 8 windows reflecting a ± 30% tolerance. These windows are (1) 0.5% – 1.0%; (2) 1.0% – 2.0%; (3) 2.0% – 4.0%; (4) 4.0% – 8.0%; (5) 8.0% – 16%; (6) 16% – 32%; (7) 32%

− 64%; and (8) 64% − 100%. It should be noted that the window of highest abundance is truncated since no peak can have an abundance greater than 100%. It is seen that any abundance value within one of these windows is within ± 30% of the center value thereof. A similar breakdown of the abundance range can be done with respect to other tolerances, such as, for example, ± 10%, ±20% and ±50%.

It is assumed that it is equally probable that the abundance of a measured mass peak will fall within one of the aribtrarily defined tolerance windows. (A more sophisticated approach might consider that the probability of a measured abundance falling within a particular tolerance window is a variable, and a determination made of that probability function by a study of the library of spectral data comprising the universe of interest.) In any event, the probability that an observed peak will fall within the correct or predicted abundance window by chance is 1 in $n$, where $n$ is the number of windows in the abundance range (a function of the tolerance as described above). Thus the window tolerance, W, is defined as the logarithm to the base 2 of $n$. The values of W as a function of tolerance is shown in the following Table 2:

Table 2

| Tolerance | n | W |
| --- | --- | --- |
| ± 10% | 32 | 5 |
| ± 20% | 16 | 4 |
| ± 30% | 8 | 3 |
| ± 50% | 4 | 2 |

If, at the jth mass position, the measured mass peak abundance (intensity) falls within the tolerance window of the predicted mass peak abundance, the "closeness" of the match is a function of the tolerance. The smaller the tolerance, the higher the probability that sample is the target compound (since the relative intensity patterns appear to match). The W value reflects this probability function by being additive to the value of $V_j$ (i.e., $U_j - A_j$).

The magnitudes chosen for $U_j$ and $A_j$ are based on the spectra of pure compounds. However, if the target compound represents only part of the sample, its actual abundance (and thus the uniqueness) of its peaks will be reduced. In such a case, the uniqueness contribution to K of each peak should be less than $V_j$. Thus, if a mass peak measured for an unknown sample is due, in part, to a second compound, the abundance factor must be reduced by a dilution factor D, the latter being subtracted from the $V_j$ values for each peak of the target compounds contracted spectrum. Thus, the dilution factor D is based on the quantity of the target compound found Q relative to the quantity of the sample, Qs, introduced into the system, typically a standard quantity. The dilution factor D is defined as follows:

$$D = - \log_2(Q/Q_s) \qquad 7.$$

If $Q = Q_s$, the sample is pure, and $D = 0$. For mixtures, Q is less than $Q_s$. The definition of D is based on the observation that if there are $2^D$ different compounds present in the sample in equal amounts, the observed quantity of any one compound would be reduced by the factor $2^D$ and there would be about $2^D$ times as many peaks of any given intensity than if the sample were pure.

With reference to the generation of the confidence index K, consider the first mass peak. For that peak, $K_1$ equals $V_1 - D_1$; ($W_1$ equals zero since the first peak must serve as the reference for predicting the abundance of the next peak). The value of $V_j$ at each mass position in the spectra of the target compounds is stored in analysis memory means 98. Thus, if a first mass peak is measured, spectral matching means 100 obtains the value of $V_1$ from analysis memory means 98. The value of $D_1$ is then determined from the maximum estimated quantity of the target compound Q and the known quantity of the sample $Q_s$, in accordance with equation (7), and subtracted from the value of $V_1$.

Next, the intensity of the second mass peak is measured. If its intensity is within the window tolerance of its predicted value (based upon the intensity of the first peak), $K_2$ equals $V_2 - D_1 + W$. $D_1$ and $D_2$ should be approximately equal since the estimate of the quantity of the target compound from the intensity of the second peak should be about the same as that estimated from the intensity of the first peak. The value of $V_2$ is obtained from analysis memory means 98 and the value of $K_2$ determined by substracting therefrom the values of $D_1$ and W, the latter in accordance with Table 2. At this point the overall confidence index, $K_1$, equals $K_1 + K_2$.

If the intensity of the second peak is greater than the value predicted by more than the window tolerance, the second mass peak is deemed to be contaminated and $K_2$ is set equal to zero. If, on the other hand, the intensity of the second peak is below the predicted intensity value by more than the window tolerance, the intensity of the second peak becomes the new reference peak, and a value of the intensity of the first peak is then predicted again on the basis of the intensity of the second peak and the stored spectral data of the target compound sought (which data reflects the relative intensities of the various peaks thereof). The measured value of the intensity of the first peak is next checked to determine whether it exceeds the predicted value by more than the window tolerance. If it does, the first peak is deemed contaminated and $K_1$ is set to zero. $K_2$ then becomes equal to $V_2 - D_1$, $W_2$ being set to zero since the second peak is now the reference peak. The measured intensities for all subsequent peaks are treated in the same manner by spectral matching means 100. Thus, if $I_j$, the intensity measured at the jth mass position is below the predicated intensity value, the intensities of all previous uncontaminated peaks are rechecked against the new reference intensity $I_j$. Any previous peaks which are now above the allowed window tolerance are termed contaminated, and their K values are reduced to zero. The K values of the other peaks must be recalculated to reflect the new value of $D_j$, and then K is redetermined.

If measured intensity $I_j$ is equal to or less than the background intensity at the jth mass position, $B_j$, $K_j$ is set to zero. However, if $B_j$ if lower than the intensity predicted by the reference peak, the intensity of the jth peak is assumed to be $B_j$ and the intensities of all previous peaks rechecked based upon the intensity value of $B_j$ as the reference peak. The final confidence index K equals the summation of the individual $K_j$ values. Spectral matching means 100 does the summation of $K_j$ values after the last measurement is made at the last mass position in the contracted mass spectrum of the target compound.

The final value of confidence index K is output from spectral matching means 100 to a suitable display which is part of conventional input/output means 104. This confidence index informs the operator that, on average, $2^K$ compounds in the universe of interest would have to be selected at random and examined in order to find data which would match the target compound's contracted spectrum to the same degree as does the unknown sample.

QUANTITATION

After contaminated peaks are eliminated, spectral matching means 100 estimates the quantity, Q of the target compound identified. One method for doing this is to average the values of the estimated quantity, $Q_j$, determined at each uncontaminated peak. Thus, $$Q = \frac{1}{m} \sum_{j=1}^{m} Q_j$$

Alternatively, the quantity Q could be determined from the intensity of the peak finally used as the reference peak. The quantity based upon the reference peak intensity must be considered a maximum value, since this peak could be contaminated. However, the probability of such contamination will be small if the confidence index K is relatively high.

MODES OF OPERATION

The preferred embodiment of this invention is capable of operating in four basic modes; (i) start-up; (ii) calibration; (iii) identification; (iv) data system. Mode selection is done via conventional switches on input/output means 104.

In the start-up mode, proper operating temperatures of the sample inlet device 10 are established; the separator 20 and the mass spectrometer 12 are evacuated; the system sensitivity is established by the parameter determination means 96; and the mass scan converter scale factor and offset corrections are made so as to enable accurate mass peak measurements. Other necessary preliminary functions are also carried out by control means 14 and/or by the operator.

In the calibration mode, the intensities of the contracted reference spectrum for each target compound are measured and stored in the analysis memory means 98. A known sample quantity of each target compound is first injected into the sample inlet device 10. The calibration is then performed as follows:

The first mass in the identification set is repeatedly measured, with appropriate adjustments in system sensitivity to keep the peak on scale. When the intensity of the first mass peak exceeds the stored background intensity at that mass position, by a specified factor, the intensity of the peak is monitored until it reaches a maximum and begins to decrease. At this point the remaining masses in the set are measured in sequence and stored, after subtracting the corresponding stored background intensities.

The relationship between the intensities of the mass peaks measured and the known quantity of the calibration sample is used by spectral matching means 100 to determine the system response sensitivity at each mass position in the contracted mass spectrum of the target compound. Thus, if the intensity of the jth mass is $I_j$, and the calibration quantity is $Q_c$, the sensitivity of the jth mass to the target compound is $S_j = I_j/Q_c$. The values of $S_j$ are stored in analysis memory means 98 and used in the identification mode to determine estimated quantities of the target compound present, as described above.

The measurement of background intensities, as described above, can be considered to be done in the calibration mode. However, the system must, of course, be purged of any residual sample material.

The identification mode is used to assay samples for the presence of one or more of the target compounds. It is subdivided into a confirmation mode and a search mode.

In the confirmation mode, the invented system is used to confirm the presence of a single target compound. Thus, the mass analysis to determine K and Q described above is run repeatedly for a period of time determined by the operator (through input/output means 104), during which time the sample is introduced. The highest values of K and Q are retained as the final confidence index and quantity estimates. This value of K is compared with a predetermined threshold value $K_T$; if K exceeds $K_T$, the identification is positive; that is, the target compound is indicated to be present in the sample. The amount of the target compound estimated to be contained in the sample is the final Q value. The results of the analysis are then displayed on a display position of input/output means 104, preferably on a set of illuminated indicators labeled with the names of the target compounds. If one of the target compounds is identified, the corresponding indicator is illuminated. The result may also be printed out, if desired, on a conventional teletype. In addition, the confidence index, mass peak intensities and quantity found may be displayed and/or printed out.

In the search mode, each target compound in the entire set of target compounds, or a subset thereof, is searched for sequentially in the sample. For each compound sought, the spectral analysis of the sample is carried out as described above, with two exceptions: first, the spectral analysis is terminated by spectral matching means 100 with respect to any target compound sought if (a) the confidence index K, based upon the peaks analyzed to that point, exceeds a threshold index $K_T$; or (b) the quantity estimate of the target compound at any time is less than a threshold quantity $Q_T$. In the former case, the identification is deemed to be sufficiently positive. In the latter case, the identification is deemed to be negative because the target compound is not present in a sufficient quantity. When the spectral analysis is terminated under either of the foregoing conditions, spectral matching means 100 issues a "skip to next compound" signal to the parameter determination means 96, causing the latter to proceed to the next target compound; i.e., to analyze the sample at the mass positions of the next target compound's contracted spectrum. If an identification of a target compound is positive, the quantity estimate thereof is the maximum estimated at any peak satisfying the condition, $K \geq K_T$.

By proper selection of the mass peaks used in the identification, it is usually possible that only one, or at most a few, peaks need be examined to establish the absence of a target compound. As a result, the present invention can analyze a sample and search a plurality of target compounds for an identification match in a relatively short time. For example, 16 target compounds can be searched in much less time than that normally required to measure once the entire mass spectrum (e.g. 400 amu) of the sample.

As in the confirmation mode, illuminated indicators and an optional printout may be used to convey the results of the analysis to the operator. When no positive identification occurs, the operator may then proceed to the next sample.

In the identification mode, the input/output means 104 permits the operator to select the target compound or compounds to be confirmed or sought, in the sample.

In the data system mode, the present invention can be used to generate new or special compound identification programs, as well as for conventional mass spectrometry or mass fragmentography applications. In this mode, one can rapidly scan all or part of a mass spectrum in any sequence, print or plot results, and analyze the data to derive a contracted mass spectrum.

First, the control memory means 92 is loaded with all or a portion of the known mass positions found in the spectrum of a particular compound. A known quantity of a pure sample of the compound is then injected into the sample inlet device 10 and the mass peak intensities are measured at each of the mass positions stored. Measurements can be made repeatedly or at the operator's request. The measured mass intensities are corrected by subtraction of the background intensities present in the system.

For each mass peak measured, spectral matching means 100 looks up the uniqueness factor $U_j$, stored in analysis memory means 98. In addition, based upon the relative intensity of each mass peak measured, the abundance factor $A_j$ is also determined for each peak from Table I, which is also stored in analysis memory means 98. Spectral matching means 100 reduces the value of each $U_j$ factor by the corresponding abundance factor $A_j$ to yield a $V_j$ value; as indicated above, $V_j = U_j - A_j$. The values of $V_j$, $I_j$ and $S_j$ at each mass peak measured are displayed through the input/output means 104. The operator may then select the most unique mass peaks (i.e., those having the highest values of $V_j$) to make up the contracted mass spectrum of the compound measured. The spectral data of the contracted mass spectrum of that compound may then be stored in control memory means 92 and analysis memory means 98 for subsequent use in identifying that compound in an unknown sample. This invention also contemplates the automatic selection of the most unique mass peaks based upon one or more pre-stored selection criterion, and the automatic storage of such selected mass peaks in memory means 92 and 98. Thus, in the data system mode, any compound of interest may be analyzed and the necessary spectral data obtained to enable that compound to be made a target compound in the invented system. In this manner, the operator can develop his own set of target compound spectra.

Figure 12:
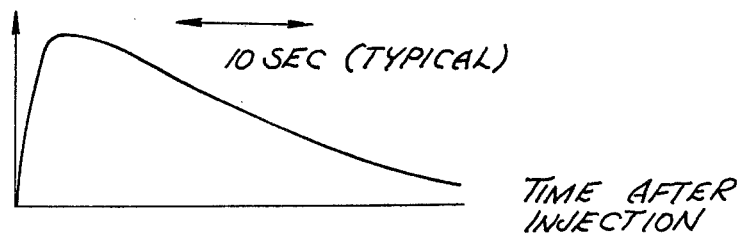
FIG. 12 shows a time profile of the sample partial pressure after injection into the sample inlet device.

Operation of the invented system in the calibration, identification and data system modes requires introduction of the sample into the sample inlet device 10. Samples are introduced in such a way that the partial pressure of the sample vapor in the mass spectrometer is maintained at a level sufficient for detection above the spectrometer background for the 1 to 10 seconds required to perform an analysis. The temperatures of the flash evaporator 18 and separator 20, the carrier gas flow rate and the vacuum system pumping speeds are chosen so that the partial pressure of the sample vapor in the mass spectrometer ion source has the general time behavior shown in FIG. 12. Gaseous samples may be valved into the carrier gas stream so as to produce a similar pressure pattern.

A number of variations on the structure and operation of the present invention are possible without departing from its essential scope and spirit. Some of the possible variations are described as follows:

1. The analysis of data for identification purposes could be done "off-line" rather than in real time. That is, the data could be measured and stored, and analyzed later.
2. An alternate comparison or matching method could be used, such as, for example, the "Biemann - MIT" system which utilizes the two largest peaks in each 14 mass unit interval (described by Hertz, Hites, and Biemann in Analytical Chemistry Vol. 43, page 681 (1971)).
3. The entire spectrum, rather than a partial spectrum, could be measured. For each compound of interest the appropriate measurements could be extracted and compared with the reference data.
4. Identification data generation, as described with respect to the data system mode above, could be made entirely automatic. That is, an unknown sample (pure or mixture) could be introduced and, in lieu of the operator, the system could be designed to select the most appropriate (highest $V_j$) peaks for the contracted mass spectrum. The spectral data associated with such peaks would then be stored for use in the subsequent assay of unknown samples.

The inventive principles embodied in the present invention are also applicable to other physical measurement methods which produce a "spectrum" or a pattern of characteristic relative intensities as a function of some parameter. Examples of such physical measurements include emission and absorption optical spectrometry (ultraviolet, visible, infrared), nuclear magnetic resonance and X-ray spectrometry.

Although this invention has been disclosed and described with reference to a particular embodiment, the principles involved are susceptible of other applications which will be apparent to persons skilled in the art. This invention, therefore, is not intended to be limited to the particular embodiment herein disclosed.

We claim:

1. In a mass spectrometric system comprised of (i) means for measuring the mass spectra of sample compounds; (ii) means for introducing a sample of a pure compound or a mixture of compounds into said measuring means; (iii) means for controlling the operation of said measuring means so as to measure the intensities of one or more mass peaks of said sample; and (iv) means for data input and output electrically coupled to said control means and to means for analyzing said mass peaks, said analysis means comprising:

a. first means for storing the mass spectrum of at least one target compound or a contracted mass spectrum thereof;
    b. second means for storing at least one spectral matching criterion;
    c. means for matching said measured mass peaks to corresponding mass peaks of said stored spectrum of said target compound on a probabilistic basis, the degree of said matching being determined with respect to said spectral matching criterion, said matching means being electrically coupled to said first and second storage means and to said measuring means, whereby, said target compound is identified as being present in said sample or as not being present therein in accordance with said spectral matching criterion.

2. The invention of claim 1 wherein the presence or absence of said target compound is confirmed by said matching means by a plurality of matching cycles.

3. The invention of claim 1 wherein the mass spectra of a plurality of target compounds, or contracted spectra thereof, are stored in said first storage means, and wherein the presence or absence of all or a subset of said target compounds is determined by said matching means, said matching means matching said measured mass peaks to the corresponding mass peaks of said stored spectra of each of said target compounds, or subset thereof.

4. The invention of claim 1 wherein said matching means comprises:
 i. means for determining a probabilistic measure of the likelihood of the presence of said target compound based upon said measured mass peaks, said determination means being electrically coupled to said first storage means and said measuring means; and
 ii. first means for comparing said probabilistic measure to said spectral matching criterion, said comparison means being electrically coupled to said determination means and said second storage means.

5. The invention of claim 4 wherein said matching means has in addition thereto third means for storing a uniqueness factor for each mass peak in said mass spectrum of said target compound, said uniqueness factor reflecting the number of randomly selected mass spectra from a universe of compounds of interest which would have to be examined to find one having said mass peak, said third storage means being electrically coupled to said means for determining a probabilistic measure, said determination means determining, for each of said measured mass peaks, the corresponding uniqueness factor thereof and operating upon said factors to determine said probabilistic measure.

6. The invention of claim 4 wherein said matching means has in addition thereto second means for comparing the relative intensities of said measured mass peaks to the corresponding relative intensities of the mass peaks of said target compound's spectrum, said second comparison means being electrically coupled to said first storage means, said measuring means and to said means for determining a probabilistic measure, said mass spectrum of said target compound, stored in said first storage means, including the relative intensities of the mass peaks comprising said spectrum, and said determination means being arranged and configured to adjust said probabilistic measure based upon said comparison of said relative intensities.

7. The invention of claim 6 wherein said means for comparing relative intensities is arranged and configured to apply a tolerance window in making said comparisons.

8. The invention of claim 4 wherein said matching means has in addition thereto means for determining a measure of the quantity of said target compound in said sample, said quantity determination means being electrically coupled to said measuring means and said means for determining a probabilistic measure, said measure determination means being arranged and configured to adjust said probabilistic measure based upon said measure of quantity.

9. The invention of claim 4 wherein said matching means has in addition thereto:
 i. third means for storing a uniqueness factor for each mass peak in said mass spectrum of said target compound, said uniqueness factor reflecting the number of randomly selected mass spectra from a universe of compounds of interest which would have to be examined to find one having said mass peak, said third storage means being electrically coupled to said means for determining a probabilistic measure; and
 ii. second means for comparing the relative intensities of the mass peaks of said target compound's spectrum, said second comparison means being electrically coupled to said measuring means, said first storage means and to said means for determining a probabilistic measure, said mass spectrum of said target compound, stored in said first storage means, including the relative intensities of the peaks comprising said spectrum,
said determination means determining, for each of said measured mass peaks, the corresponding uniqueness factor thereof, and being arranged and configured to determine said probabilistic measure based upon said uniqueness factors and the comparison of said relative intensities.

10. The invention of claim 4 wherein said matching means has in addition thereto.
 i. third means for storing a uniqueness factor for each mass peak in said mass spectrum of said target compound, said uniqueness factor reflecting the number of randomly selected mass spectra from a universe of compounds of interest which would have to be examined to find one having said mass peak, said third storage means being electrically coupled to said means for determining a probabilistic measure; and
 ii. means for determining a measure of the quantity of said target compound in said sample, said quantity determination means being electrically coupled to said measuring means and said means for determining a probabilistic measure, said determination means determining, for each of said measured mass peaks, the corresponding uniqueness factor thereof, and being arranged and configured to determine said probabilistic measure based upon said uniqueness factors and said measure of quantity.

11. The invention of claim 4 wherein said matching means has in addition thereto:
 i. third means for storing a uniqueness factor for each mass peak in said mass spectrum of said target compound, said uniqueness factor reflecting the number of randomly selected mass spectra from a universe of compounds of interest which would have to be examined to find one having said mass peak, said third storage means being electrically coupled to said means for determining a probabilistic measure;
 ii. second means for comparing the relative intensities of said measured mass peaks to the corresponding relative intensities of the mass peaks of said target compound's spectrum, said second comparison means being electrically coupled to said measuring means, said first storage means and to said means for determining a probabilistic measure, said mass spectrum of said target compound, stored in said first storage means, including the relative intensities of the peaks comprising said spectrum; and iii. means for determining a measure of the quantity of said target compound in said sample, said quantity determination means being electrically coupled to said measuring means and said means for determining a probabilistic measure, said determination means determining, for each of said measured mass peaks, the corresponding uniqueness factor thereof, and being arranged and configured to determine said probabilisitic measure based upon said uniqueness factors, the comparison of said relative intensities and said measure of quantity.

12. The invention of claim 4 wherein the mass spectra of a plurality of target compounds, or contracted spectra thereof, are stored in said first storage means, and wherein the presence or absence of all or a subset of said target compounds is determined by said matching means, said means for determining a probabilistic measure being electrically coupled to said means for controlling said measuring means and providing thereto a "skip to next target compound" signal whenever said probabilistic measure of the likelihood of the presence of any of said target compounds exceeds a predetermined value, said control means being responsive to said signal.

13. In a mass spectrometric system, comprised of (i) means for measuring the mass spectra of sample compounds; (ii) means for introducing a sample of a pure compound or a mixture of compounds into said measuring means; (iii) means for controlling the operation of said measuring means so as to measure the intensities of one or more mass peaks of said sample; and (iv) means for data input and output electrically coupled to said control means and to means for analyzing said mass peaks, said analysis means comprising:
 a. first means for storing the mass spectrum of at least one target compound or a contracted mass spectrum thereof;
 b. second means for storing at least one spectral matching criterion;
 c. means for matching said measrued mass peaks to corresponding mass peaks of said stored spectrum of said target compound in accordance with said spectral matching criterion, said matching means being electrically coupled to said first and second storage means and to said measuring means; and
 d. third means for storing background mass peak intensities at at least the mass peak positions of said target compound's mass spectrum, said third storage means being electrically coupled to said matching means, and said matching means being electrically coupled to said means for controlling said measuring means and providing thereto a "skip to next mass" signal whenever the intensity of any measured mass peak falls below the corresponding background intensity, said control means being responsive to said signal, whereby, said target compound is identified as being present is said sample or as not being present therein in accordance with said spectral matching criterion.

14. In a mass spectrometric system comprised of (i) means for measuring the mass spectra of sample compounds; (ii) means for introducing a sample of a pure compound or a mixture of compounds into said measuring means; (iii) means for controlling the operation of said measuring means so as to measure the intensities of one or more mass peaks of said sample; and (iv) means for data input and output electrically coupled to said control means and to means for analyzing said mass peaks, said analysis means comprising:
 a. first means for storing the mass spectrum of at least one target compound or a contracted mass spectrum thereof;
 b. second means for storing at least one spectral matching criterion;
 c. third means for storing a predetermined sensitivity factor with respect to each mass peak of said target compound's sepctrum, said sensitivity factor relating the measured intensity of each mass peak to a quantity of said target compound;
 d. means for determining a measure of quantity of said target compound in said sample based upon the intensities of said measured mass peaks and said corresponding sensitivity factors, the mass peak at which the least quantity of said target compound is determined being stored in said second storage means as a reference peak, said quantity determination means being electrically coupled to said second and third storage means and to said measuring means;
 e. means for predicting the intensity of a mass peak of said sample at least one other mass position of said target compound's mass spectrum said prediction being based upon the intensity of said reference peak and said mass spectral data for said target compound, said prediction means being electrically coupled to said first and second storage means; and
 f. means for comprising the intensity of each measured mass peak to the intensity predicted therefor with respect to a predetermined tolerance, said comparison means being electrically coupled to said prediction means and to said measuring means, whereby, a mass peak is considered contaminated if its measured intensity exceeds said predicted intensity by more than said tolerance and said mass peak is considered uncontaminated if its measured intensity agress with said predicted intensity. within said tolerance, and said target compound is identified as being present in said sample or as not being present therein as a function of the number of uncontaminated mass peaks measured at mass positions of its spectrum and their uniqueness.

15. The invention of claim 14 wherein said means for predicting intensities is electrically coupled to said means for controlling said measuring means and provides thereto said predicted intensities, said control means being arranged and configured to respond thereto by adjusting the sensitivity of said measuring means to a level appropriate for the accurate measurement of each mass peak at said predicted intensity.

16. The invention of claim 14 wherein said quantity determination means estimates the quantity of said target compound in said sample by determining a measure of the quantity thereof based upon the intensity of at least one uncontaminated mass peak and the corresponding sensitivity factor at the mass position thereof.

17. The invention of claim 16 wherein said quantity determination means estimates the quantity of said target compound in said sample by averaging the measures of quantity determined at said uncontaminated mass peaks.

18. The invention of claim 16 wherein the mass spectra of a plurality of target compounds, or contracted spectra thereof, are stored in said first storage means, and wherein the presence of absence of all or a subset of said target compounds is determined, said quantity determination means being electrically coupled to said means for controlling said measuring means and providing thereto a "skip to next target compound" signal whenever said estimate of the quantity of any target compound is less than a predetermined value, said control means being responsive to said signal.

19. In a mass spectrometric system comprised of (i) means for measuring the mass spectra of sample compounds; (ii) means for introducing a sample of a pure compound or a mixture of compounds into said measuring means; and (iii) means for controlling the operation of said measuring means so as to measure the intensities of one or more mass peaks of said sample; and (iv) means for the data input and output electrically coupled to said control means and to means for anaylzing said mass peaks, said anaylsis means comprising:

a. first means for storing the mass spectrum of at least one target compound or a contracted mass spectrum thereof;

b. second means for storing at least one spectral matching criterion;

c. third means for storing a predetermined sensitivity factor with respect to each mass peak of said target compound's spectrum, said sensitivity factor relating the measured intensity of each mass peak to a quantity of said target compound;

d. means for determining a measure of quantity of said target compund in said sample based upon the intensities of said measured mass peaks and said corresponding sensitivity factors, the mass peak at which the least quantity of said target compound is determined being stored in said second storage means as a reference peak, said quantity determination means being electrically coupled to said second and third storage means and to said measuring means;

e. means for predicting the intensity of a mass peak of said sample at at least one other mass position of said target compound's mass spectrum, said prediction being based upon the intensity of said reference peak and said mass spectral data for said target compound, said prediction means being electrically coupled to said first and second storage means;

f. first means for comparing the intensity of each measured mass peak to the intensity predicted therefor with respect to a predetermined tolerance, said comparison means being electrically coupled to said prediction means and to said measuring means, a mass peak being considered contaminated if its measured intensity exceeds said predicted intensity by more than said tolerance and uncontaminated if its measured intensity agrees with said predicted intensity within said tolerance;

g. means for determining a probabilistic measure of the likelihood of the presence of said target compound based upon said uncontaminated mass peaks measured, said means for determining a probabilistic measure being electrically coupled to said first comparison means; and h. second means for comparing said probabilistic measure to said spectral matching criteria, said second comparison means being electrically coupled to said means for determining a probabilistic measure and to said second storage means, whereby, said target compound is identified as being present in said sample or as not being present therein in accordance with said spectral matching criterion.

20. The invention of claim 19 wherein said means for determining a probabilistic measure comprises:

i. fourth means for storing a uniqueness factor for each mass peak in said mass spectrum of said target compound, said uniqueness factor reflecting the number of randomly selected mass spectra from a unvierse of compounds of interest which would have to be examined to find one having said mass peak; and ii. means for calculating a confidence index electrically coupled to said fourth storage means and to said first comparison means, said calculating means determining, for each uncontaminated mass peak measured, the corresponding uniqueness factor thereof and operating upon said factors to determine said confidence index, whereby, said target compound is identified as being present in said sample if said confidence index is greater than a predetermined value thereof.

21. The invention of claim 20 wherein said calculating means adds said uniqueness factors for said uncontaminated, measured mass peaks to determine said confidence index.

22. The invention of claim 20 wherein said calculating means increases said uniqueness factor at each uncontaminated mass peak measured by a tolerance factor which reflects the tolerance within which the relative intensity of said measured mass peak matches the relative intensity of the corresponding mass peak of said target compound's spectrum.

23. The invention of claim 20 wherein said calculating means reduces said uniqueness factor at each uncontaminated mass peak measured by a dilution factor which reflects the quantity of said target compound in said sample, said calculating means being electrically coupled to said quantity determination means.

24. The invention of claim 20 wherein the mass spectra of a plurality of target compounds, or contracted spectra thereof, are stored in said first storage means, and wherein the presence or absence of all or a subset of said target compounds is determined, said calculating means being electrically coupled to said measuring means and providing thereto a "skip to next target compound" signal whenever said confidence index is greater than said predetermined value therof, said control means being responsive to said signal.

25. The invention of claim 19 wherein the presence or absence of said target compound is confirmed by said matching means by a plurality of matching cycles.

26. In a mass spectrometric system comprised of (i) means for measuring the mass spectra of sample compounds; (ii) means for introducing a sample of a pure compound or a mixture of compounds into said measuring means; (iii) means for controlling the operation of said measuring means so as to measure the intensities of one or more mass peaks of said sample; and (iv) means for data input and output electrically coupled to said control means and to means for analyzing said mass peaks, said analysis means comprising:

a. first means for storing the mass spectrum of at least one target compound or a contracted mass spectrum thereof;

b. second means for storing a uniqueness factor for each mass peak in said mass spectrum of said target compound, said uniqueness factor reflecting the number of randomly selected mass spectra from a universe of compounds of interest which would have to be examined to find one having said mass peaks;

c. means for correlating each of said measured mass peaks with a corresponding uniqueness factor, said correlation means being electrically coupled to said measuring means and to said second storage means, said correlation being displayed to an operator;

d. third means for storing at least one spectral matching criterion; and e. means for matching said measured mass peaks to corresponding mass peaks of said stored spectrum of said target compound in accordance wih said spectral matching criterion, said matching means being electrically coupled to said first and third storage means and to said measuring means, whereby, (i) a substantially pure sample of said target compound is introduced into said measuring means through said sample introduction means, said uniqueness factors are displayed for each measured mass peak of said target compound, and said operator selects mass peaks based upon at least one mass peak selection criterion and stores the same in said first storage means and said control means, and (ii) a subsequent sample of an unknown compound is introduced into said measuring means and said target compound is identified as being present in said unknown sample or as not being present therein in accordance with said spectral matching criterion.

27. The invention of claim 26 having in addition thereto:

i. fourth means for storing at last one mass peak selection criterion;

ii. means for comparing each of said uniqueness factors with said mass peak selection criterion, said comparison means being electrically coupled to said correlation means and said fourth storage means, whereby, said comparison means selects those mass peaks of said target compound which satisfy said selection criterion and stores the same in said first storage means.

28. In a compound identification system comprised of (i) means for measuring a pattern of physical characteristic of a sample compound as a function of at least one physical parameter; (ii) means for introducing a sample of a pure compound or a mixture of compounds into said measuring means; (iii) means for controlling the operation of said measuring means so as to measure said physical characteristic of said compound at one or more values of said parameters and (iv) means for data input and output electrically coupled to said control means and to means for analyzing said measured characteristics, said analysis means comprising:

a. first means for storing the known characteristic pattern of at least one target compound, or a contracted pattern thereof;

b. second means for storing at least one matching criterion; and c. means for matching said measured characteristics to corresponding characteristic patterns of said target compound on a probabilistic basis, the degree of said matching being determined with respect to matching means being electrically coupled to said first and second storage means and to said measuring means, whereby, said target compound is identified as being present in said sample or as not being present therein in accordance with said spectral matching criterion.

29. The invention of claim 28 wherein said matching means comprises:

i. means for determining a probabilistic measure of the likelihood of the presence of said target compound based upon said measured characteristics, said determination means being electrically coupled to said first storage means and said measuring means; and ii. means for comparing said probabilistic measure to said spectral matching criterion, said comparison means being electrically coupled to said determination means and said second storage means.

30. A mass spectrometric system comprising:

a. means for measuring the mass spectrum of a sample compound, said measuring means producing an ion intensity corresponding to each mass peak of said sample;

b. means for introducing a sample compound into said measuring means, said sample introduction means being in communication with said measuring means;

c. means for controlling the operation of said measuring means so as to measure the intensities of one or more mass peaks of said sample, said control means being electrically coupled to said measuring means;

d. means for converting said ion intensity into an electrical signal which is an analog of said ion intensity, said conversion means being electrically coupled to said measuring means; and e. means for analyzing said electrical signals, said analysis means comprising:

i. first means for storing the mass spectrum of at least one target compound, or a contracted mass spectrum thereof, and at least one spectral matching criterion; and ii. means for matching the mass peaks represented by said electrical signals to corresponding mass peaks of said stored spectrum of said target compound in accordance with said spectral matching criterion, said matching means being electrically coupled to said storage means, whereby, said target compound is identified as being present in said sample or as not being present therein in accordance with said spectral matching criterion.

31. The invention of claim 30 wherein said control means is arranged and configured to provide to said measuring means, for each mass peak to be measured, an electrical control signal having (i) a dc component related to a first mass position below the mass position of said mass peak to be measured and (ii) a ramp component related to a mass scan by said measuring means from said first mass position to a second mass position, said second mass position being above said mass position of said mass peak to be measured.

32. The invention of claim 30 having in addition thereto means for temporarily storing the maximum value of said electrical signal, said temporary storage means being electrically coupled between said conversion means and said analysis means, said control means being arranged and configured to provide to said temporary storage means a mode select signal prior to the measurement of each mass peak of said sample, said means for temporary storage being responsive to said mode select signal by removing said previously stored maximum value of said electrical signal.

33. The invention of claim 30 having in addition thereto means for temporarily storing the maximum value of said electrical signal, said temporary storage means being electrically coupled between said conversion means and said analysis means, and wherein said control means comprises:
 i. means for generating, for each mass peak to be measured, an electrical control signal having a dc component related to a first mass position below the mass position of each mass peak to be measured and a ramp component related to a mass scan by said measuring means from said first mass position to a second mass position, said second mass position being above said mass position of said mass peak to be measured, said control signal generating means being electrically coupled to said measuring means; and
 ii. means for generating a mode select signal electrically coupled to said temporary storage means and to said control signal generating means, said mode select generating means being arranged and configured to provide to said temporary storage means a mode select signal prior to the measurement of each mass peak of said sample, said temporary storage means being responsive to said mode select signal by removing said previously stored maximum value of said electrical signal therefrom.

34. The invention of claim 30 wherein said control means comprises:
 i. means for generating, for each mass peak to be measured, an electrical control signal related to the mass position of said mass peak to be measured, said control signal generating means being electrically coupled to said measuring means; and
 ii. means for adjusting said electrical control signal to correct for an offset in the relationship between said electrical control signal and said mass position, said adjusting means being electrically coupled to said control signal generating means.

35. The invention of claim 30 wherein said control means comprises:
 i. means for generating, for each mass peak to be measured, an electrical control signal whose amplitude is related to the mass position of said mass peak to be measured by a substantially constant scale factor over the mass range, said control signal generating means being electrically coupled to said measuring means; and
 ii. means for adjusting said electrical control signal to correct for errors in said scale factor, said adjusting means being electrically coupled to said control signal generating means.

36. The invention of claim 30 wherein said control means comprises:
 i. means for generating, for each mass peak to be measured, an electrical control signal whose amplitude is related to the mass position of said mass peak to be measured by a substantially constant scale factor over the mass range, said control signal generating means being electrically coupled to said measuring means; and
 ii. means for adjusting said electrical control signal to correct for both offset and scale factor error in the relationship between said electrical control signal and said mass position, said adjusting means being electrically coupled to said control signal generating means.

37. The invention of claim 36 wherein said means for adjusting said offset and scale factor of said electrical control signal is electrically coupled to said analysis means, said adjusting means being arranged and configured to calculate the appropriate offset and scale factor correction parameters based upon the actual values of said electrical control signals required to measure mass peaks at a plurality of known mass positions of at least one known compound introduced into said system.

38. The invention of claim 30 having in addition thereto means for temporarily storing the maximum value of said electrical signal, said temporary storage means being electrically coupled between said conversion means and said analysis means, and wherein said control means comprises:
 i. means for generating, for each mass peak to be measured, an electrical control signal having a dc component related to a first mass position below the mass position of each mass peak to be measured and a ramp component related to a mass scan by said measuring means from said first mass position to a second mass position, said second mass position being above said mass position of said mass peak to be measured, said control signal generating means being electrically coupled to said measuring means;
 ii. means for adjusting said electrical control signal to correct for both offset and scale factor error in the relationship between said electrical control signal and said mass position, said adjusting means being electrically coupled to said control signal generating means; and
 iii. means for generating a mode select signal electrically coupled to said temporary storage means and to said control signal generating means, said mode select generating means being arranged and configured to provide to said temporary storage means a mode select signal prior to the measurement of each mass peak of said sample, said temporary storage means being responsive to said mode select signal by removing said previously stored maximum value of said electrical signal therefrom;

39. The invention of claim 30 wherein said conversion means is arranged and configured to provide selectible gain.

40. The invention of claim 39 wherein said analysis means is arranged and configured to generate a rescan signal, and to provide the same to said control means, whenever the amplitude of said electrical signal is too high or too low for an accurate measure of the mass peak to which it relates, and wherein said control means is responsive to said rescan signal by (i) providing a gain select signal to said conversion means before the next measurement of a mass peak, and by (ii) repeating the measurement of said mass peak, said gain select signal being related to a gain of said conversion means which is appropriate for a more accurate measure of said mass peak, said conversion means being responsive to said gain select signal by changing its gain in accordance therewith, whereby, said system automatically establishes the appropriate gain setting of said conversion means for a accurate measure of each mass peak.

41. The invention of claim 39 wherein said conversion means comprises means for filtering said electrical signal, said filtering means having a selectible time constant, and wherein said control means comprises:
  i. means for generating an electrical control signal having a dc component related to a first mass position below the mass position of each mass peak to be measured and a ramp component related to a mass acan by said measuring means from said first mass position of a second mass position, said second mass position being above said mass position of said mass peak to be measured, said control signal generating means being electrically coupled to said measuring means, said ramp component having a selectible slope;
  ii. means for determining said filtering means time constant and said ramp slope, said determination means being electrically coupled to said conversion means and to said control signal generating means, and providing thereto time constant select and slope select signals respectively, said time constant and ramp slope being selected as a function of a gain of said conversion means, said conversion means being responsive to said time constant select signal and said control signal generating means being responsive to said slope select signal.

42. The invention of claim 41 wherein said control means has in addition thereto means for timing a delay between successive measurements by said measuring means, said timing means being electrically coupled to said control signal generating means and to said determination means, said delay being a function of a step in mass position between successive measurements, the time constant of said filtering means, the recovery time required for said conversion means following said step in mass position and the changes required of said gain and time constant settings of said conversion means.

43. The invention of claim 30 wherein:
  i. said conversion means is arranged and configured to provide selectible gain;
  ii. said alanysis means is arranged and configured to generate a rescan signal, and to provide the same to said control means, whenever the amplitude of said electrical signal is too high or too low for an accurate measure of the mass peak to which it relates, said control means being responsive to said rescan signal by providing a gain select signal to said conversion means before the mext measurement of a mass peak and by repeating the measurement of said mass peak, said gain select signal being related to a gain of said conversion means which is appropriate for a more accurate measure of said mass peak, said conversion means being responsive to said gain select signal by changing its gain in accordance therewith;
  iii. said conversion means comprises means for filtering said electrical signal, said filtering means having a selectible time constant; and
  iv. said control means comprises:
    aa. means for generating an electrical control signal having a dc component related to a first mass position below the mass position of each mass peak to be measured and a ramp component related to a mass scan by said measuring means from said first mass position to a second mass position, said second mass position being above said mass position of said mass peak to be measured, said control signal generating means being electrically coupled to said measuring means, said ramp component having a selectible slope;
    bb. means for determining said filtering means time constant and said ramp slope, said determination means being electrically coupled to said conversion means and to said control signal generating means, and providing thereto time constant select and slope select signals respectively, said time constant and ramp slope being selected as a function of the gain of said conversion means, said conversion means being responsive to said time constant select signal and said control signal generating means being responsive to said slope select signal; and
    cc. means for timing a delay between successive measurements by said measuring means, said timing means being electrically coupled to said control signal generating means and to said determination means, said delay being a function of the step in mass position between successive measurements, the time constant of said filtering means, the recovery time required for said conversion means following said step in mass position and the changes required of said gain and time constant settings of said conversion means.

44. The invention of claim 30 wherein:
  i. said conversion means is arranged and configured to provide selectible gain;
  ii. said analysis means is arranged and configured to generate a rescan signal, and to provide the same to said control means, whenever the amplitude of said electrical signal is too high or too low for an accurate measure of the mass peak to which it relates, said control means being responsive to said gain select signal by changing its gain in accordance therewith;
  iii. means for temporarily storing the maximum value of said electrical signal, included in addition thereto, said temporary storage means being electrically coupled between said conversion means and said analysis means; and
  iv. said control means comprises:
    aa. means for generating, for each mass peak to be measured, and electrical control signal having a dc component related to a first mass position below the mass position of each mass peak to be measured and a ramp component related to a mass scan by said measuring means from said first mass position to a second mass position, said second mass position being above said mass position of said mass peak to be measured, said control signal generating means being electrically coupled to said measuring means; and electrically coupled to said temporary storage means and to said control signal generating means, said mode select generating means being arranged and configured to provide to said temporary storage means a mode select signal proior to the measurement of each mass peak of said sample, said temporary storage means being responsive to said mode select signal by removing said previously stored maximum value of said electrical signal therefrom.

45. A mass spectrometric system comprising:
a. means for measuring the mass spectrum of a sample compound, said measuring means producing an ion intensity corresponding to each mass peak of said sample;
b. means for introducing a sample compound into said measuring means, said sample introduction means being in communication with said measuring means;

c. means for controlling the operation of said measuring means so as to measure the intensities of one or more mass peaks of said sample, said control means being electrically coupled to said measuring means, said control means comprising:
  i. means for generating, for each mass peak to be measured, an electrical control signal whose amplitude is related to the mass position of said mass peak to be measured by a substantially constant scale factor over the mass range, said control signal generating means being electrically coupled to said measuring means; and
  ii. means for adjusting said electrical control signal to correct for both offset and scale factor error in the relationship between said electrical control signal and said mass position, said adjusting means being electrically coupled to said control signal generating means;
d. means for converting said ion intensity into an electrical signal which is an analog of said ion intensity, said conversion means being electrically coupled to said measuring means; and
e. means for analyzing said electrical signals, said analysis means being electrically coupled to said conversion means, said analysis means comprising:
  i. first means for storing the mass spectrum of at least one target compound or a contracted mass spectrum thereof;
  ii. second means for storing at least one spectral matching criterion; and
  iii. means for matching said measured mass peaks to corresponding mass peaks of said stored spectrum of said target compound in accordance with said spectral matching criterion, said matching means being electrically coupled to said first and second
    storage means and to said conversion means, whereby, said target compound is identified as being present in said sample or as not being present in said sample or as not being present therein in accordance with said spectral matching criterion.

46. The invention of claim 45 wherein said matching means comprises:
  aa. means for determining a probabilistic measure of the likelihood of the presence of said taret compound based upon said measured mass peaks, said determination means being electrically coupled to said first storage means said conversion means, and
  bb. means for comparing said probabilistitic measure to said spectral matching criterion, said comparison means being electrically coupled to said determination means and said second storage means.

* * * * *

UNITED STATES PATENT OFFICE
CERTIFICATE OF CORRECTION

Patent No. 4,008,388             Dated February 15, 1977

Inventor(s)    Fred W. McLafferty et al.

It is certified that error appears in the above-identified patent and that said Letters Patent are hereby corrected as shown below:

Column 34, line 48, after "said" insert -- means for controlling said; --.

Signed and Sealed this

Twenty-second Day of August 1978

[SEAL]

Attest:

RUTH C. MASON
Attesting Officer

DONALD W. BANNER
Commissioner of Patents and Trademarks